United States Patent
Snyder et al.

(10) Patent No.: US 6,984,484 B1
(45) Date of Patent: Jan. 10, 2006

(54) MAMMALIAN SERINE RACEMASE

(75) Inventors: Soloman H. Snyder, Baltimore, MD (US); Herman Wolosker, Baltimore, MD (US); Kevin Sheth, Baltimore, MD (US); Takahashi Masaaki, Baltimore, MD (US); Jean-Pierre Mothet, Baltimore, MD (US); Roscoe Brady, Jr., Baltimore, MD (US); Christopher D. Ferris, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/889,609

(22) PCT Filed: Jan. 18, 2000

(86) PCT No.: PCT/US00/00938

§ 371 (c)(1),
(2), (4) Date: Dec. 12, 2001

(87) PCT Pub. No.: WO00/43526

PCT Pub. Date: Jul. 27, 2000

Related U.S. Application Data

(60) Provisional application No. 60/145,953, filed on Jul. 28, 1999, provisional application No. 60/144,839, filed on Jul. 21, 1999, provisional application No. 60/116,333, filed on Jan. 19, 1999.

(51) Int. Cl.
*C12Q 1/25* (2006.01)
*C12N 9/90* (2006.01)

(52) U.S. Cl. .......................................... 435/4; 435/233
(58) Field of Classification Search .............. 435/233, 435/252.3, 325, 320.1, 4, 252.33; 536/23.2
See application file for complete search history.

(56) References Cited

U.S. PATENT DOCUMENTS 6,458,576 B1 * 10/2002 Meyers et al. ............. 435/233

FOREIGN PATENT DOCUMENTS

GB     2048266     12/1980

OTHER PUBLICATIONS

Takuma Uo et al, "Occurrence of pyridoxal 5'-phosphate-dependent Serine racemase in silkworm, Bombyx mori" Biochemical and Biophysical Research Communications, vol. 246, No. 1, May 8, 1998.

David S. Dunlop, et al., "The origin of turnover of D-Serine in brain" Biochemical and Biophysical Research Communications, vol. 235, No. 1, Jun. 9, 1997.

Herman Wolosker et al, "Serine racemase: a glial enzyme synthesizing D-Serine to regulate glutamate-N-methyl-D-asparate neurotransmission" Proceedings of the National Academy of Sciences of USA, vol. 96, No. 23, Nov. 9, 1999, pp. 13409-13414.

Hermann Wolosker, et al., Purification of Serine racemase: "Biosynthesis of the neuromodulator D-Serine", Proceedings of the National Academy of Sciences of USA, vol. 96, No. 2, Jan. 19, 1999, pp. 721-725.

* cited by examiner

Primary Examiner—Elizabeth Slobodyansky

(74) Attorney, Agent, or Firm—Banner & Witcoff, Ltd.

(57) ABSTRACT

High levels of D-serine occur in mammalian brain, where it appears to be an endogenous ligand of the "glycine site" of NMDA receptors. We have purified from rat brain a soluble enzyme that catalyzes the direct racemization of L-serine to D-serine. Purified serine racemase has a molecular weight of 37 kDa and requires pyridoxal 5'-phosphate for its activity. The enzyme is highly selective toward L-serine, failing to racemize any other amino acid tested. We have also identified polynucleotide sequences that encode mammalian, including human, serine racemase. Compounds that modulate the activity of mammalian serine racemase are useful for treating conditions and diseases that involve overstimulation of NMDA receptors, such as stroke and various neurodegenerative diseases.

18 Claims, 8 Drawing Sheets

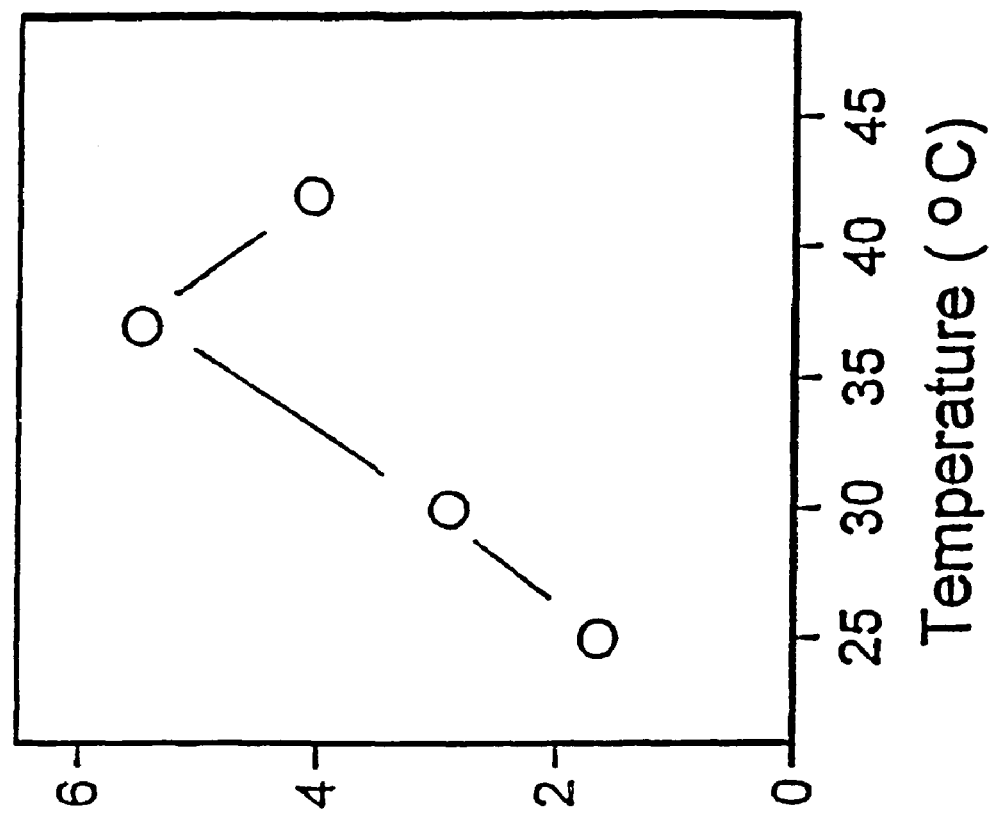
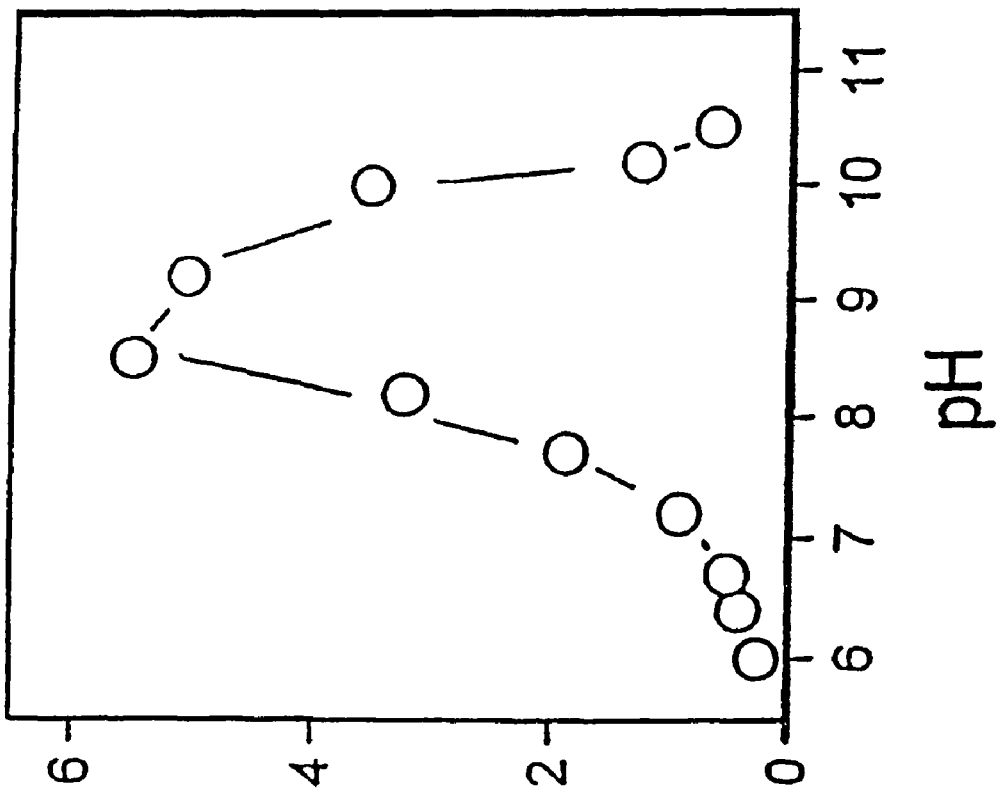
FIG. 2B
FIG. 2A

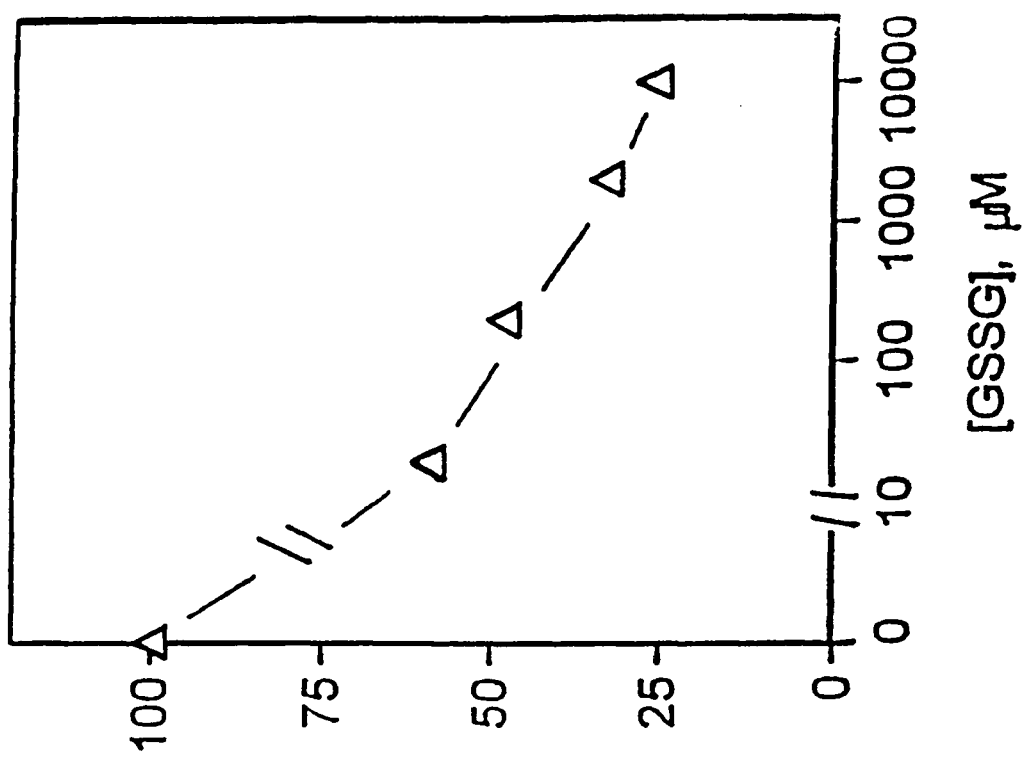
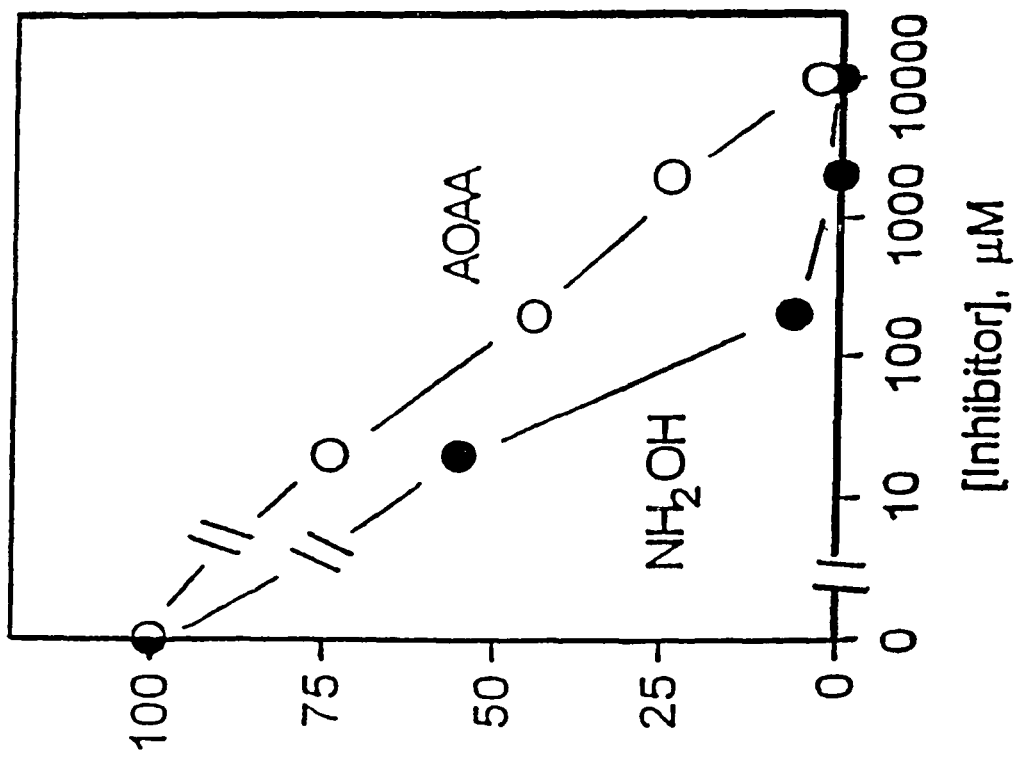
FIG. 4A
FIG. 4B

FIG. 7A

Mus musculus serine racemase gene, complete cds

Source: house mouse
Organism : Mus musculus
    Eukaryota; Metazoa; Chordata; Vertebrata; Mammalia; Eutheria;
    Rodentia; Sciurognathi; Muridae; Murinae; Mus.
Strain ="Balb/c"
Dev. Stage = Adult
Tissue type = brain Gene Starts at   219 and ends 1238

```
  1 GACCTTACAC CCTTTGCCAC ACTGGTCCTG GGCCAAGATG GGCCAATCAA AGTCCTTACC
 61 CAGAATTTTT TGAACTGAAA TTGAGAGAGA ATCCCTCTTC AGTATGGAAG CCATAAAATG
121 TAAAACACAG GAGCTGTCAG CAGCCATGTG TCCTGCAGTA CGGAGCCAGC TGGTCTGCTG
181 TGAGAAGGAA GCCGCCGTGC CAGAGGCAGC AGAGAACCAT GTGTGCTCAG TACTGCATCT
241 CCTTTGCTGA TGTTGAAAAA GCTCATATCA ACATTCAAGA CTCTATCCAC CTCACCCCAG
301 TGCTAACAAG CTCCATTTTG AATCAAATAG CAGGGCGCAA TCTTTTCTTC AAATGTGAGC
361 TCTTCCAGAA AACTGGGTCT TTTAAGATTC GAGGTGCCCT TAATGCCATC AGAGGCTTAA
421 TTCCTGACAC GCCAGAAGAG AAGCCCAAAG CCGTAGTTAC TCACAGCAGC GGAAACCATG
481 GCCAAGCTCT CACCTATGCT GCTAAACTGG AAGGAATTCC TGCTTACATT GTGGTTCCCC
541 AAACAGCTCC CAACTGCAAG AAACTGGCAA TCCAAGCCTA TGGAGCATCG ATAGTATACT
601 GTGACCCAAG TGACGAGTCC AGAGAAAAGG TCACTCAAAG AATTATGCAA GAAACAGAAG
661 GCATCTTGGT CCATCCCAAC CAGGAGCCTG CAGTGATAGC TGGACAAGGA ACAATGCCC
```

FIG. 7B

```
 721 TGGAAGTGCT GAACCAGGTT CCCTTGGTAG ATGCACTGGT GGTACCAGTA GGAGGAGAG
 781 GAATGGTTGC TGGAATAGCC ATTACAATTA AGGCCCCTGAA ACCTAGTGTG AAGTATACG
 841 CTGCTGAGCC CTCGAATGCA GATGACTGCT ACCAGTCTAA ACTGAAAGGA GAACTGACCC
 901 CCAATCTTCA TCCTCCAGAA ACCATAGCAG ATGGTGTCAA ATCCAGCATT GGCTTGAATA
 961 CCTGGCCTAT TATAAGAGAC CTTGTGGATG ATGTCTTCAC TGTCACCGAA GATGAAATCA
1021 AGTATGCAAC CCAGCTGGTG TGGGGAGAA TGAAACTGCT CATTGAGCCG ACTGCTGGCG
1081 TGGCACTGGC TGCAGTGCTG TCTCAGCATT TCCAAACAGT CTCTCCAGAA GTAAAGAACG
1141 TCTGCATTGT ACTCAGTGGG GGAATGTAG ACCTAACCTC CCTGAACTGG GTGGGCAGG
1201 CTGAACGGGC AGCTCCTTAC CAGACGGTTT CTGTTTAAAT TCAGGCAAGA TTGTCTCTAG
1261 ATGAAAATT TGTTTCCATC TTCCCTTTAA AAATTATGTT CAAAATCCTA ATGAAGAAAG
1321 TGTAAGTAAT CATGTAAATT CTGTACTTAG CAGAGACATG GACAAACTGA ATACAGAGCA
1381 CAAGCTGCCT GGTCACAACC CAGACTCCAA CACTGGAGTT TTGGTTGGTT GCAGTAGAGA
1441 CAGAACCCAA CTGAGTCTCT TACTCCATGT CTACTTCAGA CACTGTTGAA GAGATGTCAC
1501 TTTTAACCCA AGGTACTGCC TCTGGTACAT ATGGGTCATA AGTCCACTTG GGAAATACTC
1561 GCTTATAGAG ATTCATTAAT ACTGTGTCCT GAGATTTCAG CTTTCCCCAT CAAAACTGCA
1621 CTTTATATGG CCATGGGTAC CTAAAAGTTA AAACAGATAA TTGGTCAAAA AT
```

Translation:="MCAQYCISFADVEKAHINIQDSIHLTPVLTSSILNQIAGRNLFFKCELFQKTGSFKIR
GALNAIRGLIPDTPEEKPKAVTHSSGNHGQALTYAAKLEGIPAYIVVPQTAPNCKKLAIQAYGASIVYCDP
SDESREKVTQRIMQETEGILVHPNQEPAVIAGQTIALEVLNQVPLVDALVVPVGGGMVAGIAITIKALKP
SVKVYAAEPSNADDCYQSKLKGELTPNLHPPETIADGVKSSIGLNTWPIIRDLVDDVFTVTEDEIKYATQLV
WGRMKLLIEPTAGVALAAVLSQHFQTVSPEVKNVCIVLSGGNVDLTSLNWVGQAERPAPYQTVSV"

MAMMALIAN SERINE RACEMASE

This is a U.S. National Phase Application Under 35 USC 371 and applicants herewith claim the benefit of priority of PCT/US00/00938 filed Jan. 18, 2000, which was published under PCT Article 21(2) in English, and U.S. Provisional Application Ser. Nos. 60/145,953 filed Jul. 28, 1999, and 60/144,839 filed Jul. 21, 1999, and 60/116,333 filed Jan. 19, 1999.

The U.S. Government has a paid-up license in this invention and the right in limited circumstances to require the patent owner to license others on reasonable terms as provided for by the terms of USPHS grant MH-18501 and Research Scientist Award DA00074 awarded by the National Institutes of Health.

TECHNICAL AREA OF THE INVENTION

This invention relates to the area of mammalian amino acid racemase enzymes.

BACKGROUND OF THE INVENTION

D-amino acids are prominent in bacteria, and there have been occasional reports of D-amino acids in invertebrates (1, 2), whereas animal tissues were believed to contain L-amino acids exclusively. Recently, however, D-serine (3–6) and D-aspartate (7, 8) were reported in mammalian tissues, especially in the nervous system. Utilizing highly selective antibodies, we localized D-aspartate to neuroendocrine tissues (9), while the immunohistochemical localizations of D-serine closely resemble N-methyl-D-aspartate (NMDA) receptors for the neurotransmitter glutamate, consistent with chemical measurements of the distribution of D-serine (10, 11).

Glutamate cannot activate the NMDA receptor in the absence of added glycine, which indicates a "glycine site" for the receptor (12, 13). D-Serine is up to three times more potent than glycine at this site (14), suggesting that D-serine is the endogenous ligand for this site. D-Serine is localized exclusively to Type II astrocytes, a form of glia concentrated in gray matter in the same areas of the brain as NMDA receptors (10). Stimulation of the kainate subtype of glutamate receptors releases D-serine from Type II astrocytes, which implies that synaptic release of glutamate triggers release of D-serine from the astrocytes to activate NMDA receptors physiologically (10). While in most parts of the brain the distribution of D-serine resembles NMDA receptors far better than does the distribution of glycine, in some areas glycine and NMDA receptors are co-localized, suggesting that D-serine is the predominant ligand for the receptor in most brain areas but that glycine serves this purpose in some sites (11).

Activation of NMDA receptors is an important pathologic event in stroke and several neurodegenerative diseases, leading to cell death. Decreased activation of NMDA receptors can thus have a beneficial effect in the treatment of any condition or disease that includes acute or chronic neuronal death or dysfunction mediated by overactivation of NMDA receptors. Overactivation of NMDA receptors is involved in stroke, epilepsy, and chronic neurodegenerative diseases such as Parkinson's disease, Huntington's disease, motor neuron diseases, and Alzheimer's disease. Thus, there is a need in the art to determine how D-serine is formed in the brain, so that its concentration in NMDA-related diseases can be regulated.

SUMMARY OF THE INVENTION

It is an object of this invention to provide isolated mammalian serine racemase protein and polynucleotide molecules, as well as methods of producing these molecules. These and other objects of the invention are provided by one or more of the embodiments described below.

One embodiment of the invention is a preparation of an isolated mammalian serine racemase having a specific activity of at least 0.003 $\mu$mole L-serine/mg/hour.

Another embodiment of the invention is an isolated and purified polynucleotide molecule which encodes a mammalian serine racemase.

Still another embodiment of the invention is a host cell comprising an expression construct which comprises a polynucleotide molecule encoding a murine serine racemase.

Even another embodiment of the invention is a method of producing a mammalian serine racemase. A host cell comprising an expression construct which comprises a polynucleotide molecule encoding a mammalian serine racemase is cultured in a culture medium. Mammalian serine racemase is recovered from the culture medium or the host cell.

Yet another embodiment of the invention is a method to screen compounds to identify candidate therapeutic agents. A test compound is contacted with a mammalian serine racemase. Activity of the mammalian serine racemase is assayed. A test compound is identified as a candidate therapeutic agent if it modulates the activity of the mammalian serine racemase.

The invention thus provides mammalian serine racemase molecules, polynucleotide sequences encoding the molecules, host cells, methods of producing mammalian serine racemase, and methods of screening test compounds to identify modulators of mammalian serine racemase. Modulators of mammalian serine racemase molecules can be used therapeutically, inter alia, to treat acute or chronic neural death or dysfunction mediated by overactivation of NMDA receptors.

BRIEF DESCRIPTION OF THE DRAWINGS

FIG. 2. pH and temperature-dependence of racemase activity. FIG. 2A. Racemase activity was assayed at 37° C. in media containing 50 mM MES-Tris (pH 6.0 to 6.5), 50 mM Tris-HCl (pH 6.8 to 8.8) of 50 mM CAPS-NaOH (pH 9 to 10,5), 20 mM L-serine. 40–100 $\mu$g/ml purified enzyme, 1 mM EDTA, 2 mM DTT, and 15 $\mu$M pyridoxal 5'-phosphate. FIG. 2B. Racemase activity was assayed at different temperatures in a medium containing 50 mM Tris-HCl (pH 8.0), 20 mM L-serine, 40–100 $\mu$g/ml purified enzyme, 1 mM EDTA, 2 mM DTT, and 15 $\mu$M pyridoxal 5'-phosphate. The reaction was stopped after 4 hours and analyzed by both chemiluminescence and HPLC assay. The experiment was replicated three times using different preparations with similar results.

FIG. 4. inhibition of serine racemase by PLP inhibitors and sulfhydryl oxidation. FIG. 4A. Enzyme activity was monitored at 37° C. in a medium containing 50 mM Tris-HCl (pH 8.0), 20 mM L-serine, 40–100 µg/ml purified enzyme, 1 mM EDTA, 2 mM DTT, 10 µM pyridoxal 5'-phosphate and different concentrations of either aminooxyacetic acid (○) or hydroxylamine (●). FIG. 4B. Reaction medium and conditions were as described in A, except that DTT was omitted from the last step of the enzyme preparation. The enzyme was preincubated for 10 minutes in the presence of different concentrations of oxidized glutathione (GSSG).

FIG. 7. Complete coding sequence of mouse serine racemase (SEQ ID NO:11) and its translated amino acid sequence (SEQ ID NO:8).

DETAILED DESCRIPTION OF THE INVENTION

The inventors' isolation of serine racemase represents the first purification of an enzyme which converts L-serine to D-serine. Bacteria contain substantial levels of D-serine and many other D-amino acids. Though a number of amino acid racemases have been purified for bacteria, no serine-specific enzyme has been previously identified (19–21).

Serine racemase appears to be a very conserved enzyme. For example, the pH optimum in the rat brain enzyme we have purified, as well as its requirement for PLP and behavior in chromatographic systems, resemble the activity characterized in crude preparations of silkworm (18). Bacterial amino acid racemases display properties resembling serine racemase including $K_m$ values, alkaline pH optimum, and the requirement for PLP. The alkaline pH optimum, might reflect the mechanism of racemization, as PLP non-enzymatically racemizes amino acids at alkaline pH (22).

Serine racemase displays a $K_m$ value in the direction L- to D-serine which resembles brain levels of L-serine and which favors the physiologic synthesis of D-serine. Because of the much higher $K_m$ value in the direction D- to L-serine, under physiological conditions the enzyme should predominantly make D-serine.

Mammalian serine racemase can be isolated from homogenates of mammalian brain, such as rat, mouse, or preferably human brain. Other forms of mammalian serine racemase can be isolated from brain homogenates of other mammals, such as monkey, pig, cow, sheep, goat, guinea pig, and the like. The enzyme can be purified, partially or to homogeneity, using all or part of the method described in Example 1. This method employs, sequentially, ammonium sulfate fractionation, butyl-sepharose, Q-sepharose, mon-Q, and hydroxyapatite chromatography steps (Table 1).

Preferably, a preparation of isolated mammalian serine racemase is able to convert L-serine to D-serine with a specific activity of at least 0.003, 0.025, 0.075, 1, 2.5, or 5 µmole of L-serine/mg/hr. The specific activity of isolated mammalian serine racemase can be determined inter alia by the assay described in Example 2. Other methods as are known in the art can also be employed.

Figure 5:
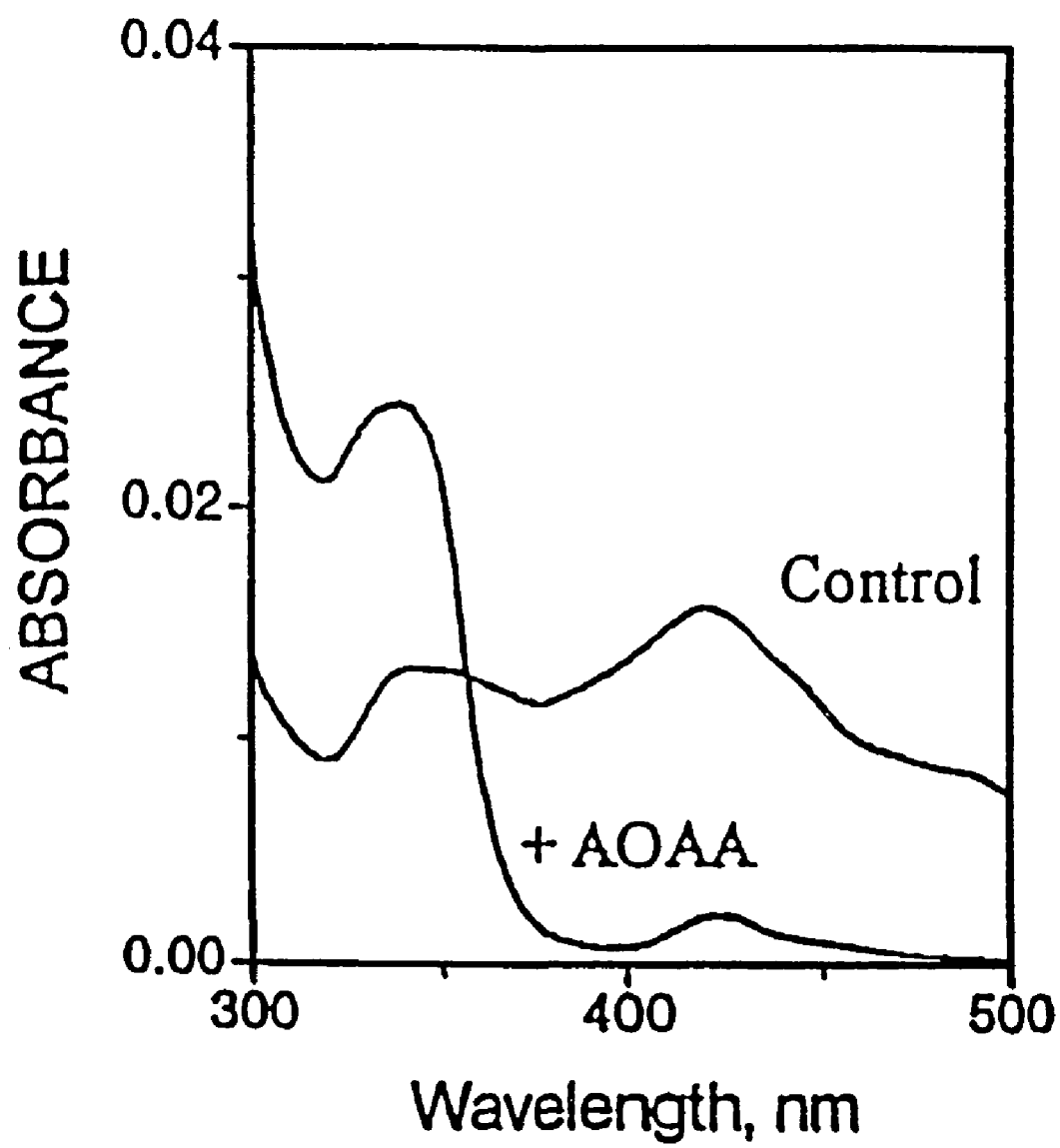
FIG. 5. Absorption spectra of purified serine racemase. Purified enzyme (70 µg/ml) was preincubated for 10 minutes in medium containing 10 mM KPi (pH 7.2), 2 mM DTT, 1 mM EDTA, 10 µM PLP, either in the absence (Control) or in the presence of 1 mM aminooxyacetic acid (AOAA). The distinct peaks of absorbance at 420 and 340 nm were not observed in the presence of buffer alone or when bovine serum albumin was used instead of serine racemase.

Serine racemase is a relatively small soluble protein of 37 kDa Murine serine racemase has the amino acid sequence shown in SEQ ID NO: 8. Rat serine racemase comprises the amino acid sequences shown in SEQ ID NOS: 6 and 7. Human serine racemase comprises amino acid sequences encoded by the nucleotide sequences shown in SEQ ID NO: 2, 3, or 9. The protein contains a pyridoxal 5' phosphate binding region (ELFQKTGSFKIRGA, amino acids 47–60 of SEQ ID NO: 8), which supports the biochemical prediction that the serine racemase is a pyridoxal phosphate binding protein (FIGS. 4 and 5).

The invention also provides polypeptide fragments of mammalian serine racemase. Polypeptide fragments may contain less than full-length mammalian serine racemase and can contain at least 6, 8, 10, 13, 25, 27, 50, 100, 121, 150, 200, 250, or 300 contiguous amino acids selected from SEQ ID NOS: 6, 7, 8, or 10 or amino acid sequences encoded by the nucleotide sequences shown in SEQ ID NO: 1, 2, 3, or 9. One such polypeptide fragment is the pyridoxal 5' phosphate binding region (amino acids 47–60 of SEQ ID NO: 8). Other polypeptide fragments of interest can be identified using routine protein analysis techniques known in the art. These techniques include, but are not limited to, hydrophobicity and hydrophilicity plots, homology searches for various motifs, antigenic indices, and standard algorithms such as those disclosed in Harlow & Lane, ANTIBODIES— A LABORATORY MANUAL (Cold Spring Harbor Laboratory, 1988). Enzymes can be used to generate mammalian serine racemase polypeptides by enzymatic proteolysis of full-length mammalian serine racemase. Polypeptide fragments can be used to generate antibodies, which in turn can be used to localize the racemase in tissues.

Mammalian serine racemase protein and polypeptides can also be produced by recombinant DNA methods or by synthetic chemical methods. For production of recombinant serine racemase, coding sequences such as those selected from the nucleotide sequences shown in SEQ ID NOS: 1, 2, 3, or 9 can be expressed in known prokaryotic or eukaryotic expression systems. Bacterial, yeast, insect, or mammalian expression systems can be used, as is known in the art.

Alternatively, synthetic chemical methods, such as solid phase peptide synthesis, can be used to synthesize mammalian serine racemase protein or polypeptides. General means for the production of peptides, analogs or derivatives are outlined in B. Weinstein, ed., CHEMISTRY AND BIOCHEMISTRY OF AMINO ACIDS, PEPTIDES, AND PROTEINS—A SURVEY OF RECENT DEVELOPMENTS (1983).

Mammalian serine racemase proteins, however produced, can contain alterations in amino acid sequence relative to the amino acid sequences encoded by SEQ ID NOS: 1, 2, 3, or 9 which do not affect the serine racemase activity of the protein. Guidance in determining which amino acid residues may be conservatively substituted, inserted, or deleted without abolishing serine racemase activity can be found using computer programs well known in the art, such as DNAS-TAR software. Whether an amino acid change results in a functional serine racemase can readily be determined by assaying serine racemase activity as described in Example 2.

Preferred mammalian serine racemase proteins have amino acid sequences which are at least 85%, 90%, 95%, 96%, or 97% identical to the amino acid sequences encoded by a polynucleotide having a coding sequence as shown in SEQ ID NOS: 1, 2, 3, or 9. More preferably, the molecules are at least 98% or 99% identical. Percent identity is determined according to the Smith-Waterman homology search algorithm, using an affine gap search with the following parameters: a gap open penalty of 12 and a gap extension penalty of 1. The Smith-Waterman homology search algorithm is taught in Smith and Waterman, Adv. Appl. Math. (1981) 2: 482–489.

Fusion proteins comprising at least 6, 8, 10, 13, 25, 27, 50, 100, 121, 150, 200, 250, or 300 contiguous amino acids selected from SEQ ID NOS: 6, 7, 8, or 10 or amino acid sequences encoded by SEQ ID NO: 1, 2, 3, or 9 can also be constructed. Fusion proteins are useful for generating antibodies against mammalian serine racemase amino acid sequences and for use in various assay systems. For example, mammalian serine racemase fusion proteins can be used to identify proteins which interact with the enzyme and which influence its racemase activity. Physical methods, such as protein affinity chromatography, or library-based assays for protein-protein interactions, such as the yeast two-hybrid or phage display systems, can also be used for this purpose. Such methods are well known in the art and can also be used to screen drugs.

A mammalian serine racemase fusion protein comprises two protein segments fused together by means of a peptide bond. The first protein segment consists of at least 6, 8, 10, 13, 25, 27, 50, 100, 121, 150, 200, 250, or 300 contiguous amino acids selected from SEQ ID NOS: 6, 7, 8, or 10 or amino acid sequences encoded by SEQ ID NO: 1, 2, 3, or 9. The first protein segment can also be a full-length mammalian serine racemase protein. The first protein segment can be N-terminal or C-terminal, as is convenient.

The second protein segment can be a full-length protein or a protein fragment or polypeptide. Proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Epitope tags can be used in fusion protein constructions, including histidine (His) tags, FLAG tags (Kodak), influenza hemagglutinin (HA) tags, Myc tags, VSV-G tags, and thioredoxin (Trx) tags. Other fusion constructions can include maltose binding protein (MBP), S-tag, Lex A DNA binding domain (DBD) fusions, GAL4 DNA binding domain fusions, and herpes simplex virus (HSV) BP16 protein fusions.

Mammalian serine racemase fusion proteins can be made by covalently linking the first and second protein segments or by standard procedures in the art of recombinant DNA technology. Recombinant DNA methods can be used to prepare fusion proteins, for example, by making a DNA construct which comprises coding sequences selected from SEQ ID NOS: 1, 2, 3, or 9 in proper reading frame with nucleotides encoding the second protein segment and expressing the DNA construct in a host cell, as is known in the art. Many kits for constructing fusion proteins are commercially available from companies such as Promega Corporation (Madison, Wis.), Stratagene (La Jolla, Calif.), Clontech (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Isolated mammalian serine racemase proteins, polypeptides, or fusion proteins can be used as immunogens, to obtain a preparation of antibodies which specifically bind to epitopes of mammalian serine racemase. The antibodies can be used, inter alia, to detect mammalian serine racemase in mammalian brain tissue or in fractions thereof. The antibodies can also be used to detect the presence of mutations in a gene encoding a mammalian serine racemase which result in under- or over-expression of the enzyme or in expression of an enzyme with altered size or electrophoretic mobility. Antibodies can also be used therapeutically, to decrease the specific activity of the serine racemase, as described below.

Antibodies which specifically bind to epitopes of mammalian serine racemase proteins, polypeptides, or fusion proteins can be used in immunochemical assays, including but not limited to Western blots, ELISAs, radioimmunoassays, immunohistochemical assays, immunoprecipitations, or other immunochemical assays known in the art provide a detection signal in immunoassays such as which is at least 5-, 10-, or 20-fold higher than a detection signal provided with other proteins when used in such immunochemical assays. Preferably, antibodies which specifically bind to mammalian serine racemase epitopes do not detect other proteins in immunochemical assays and can immunoprecipitate the enzyme or fragments thereof from solution.

Mammalian serine racemase-specific antibodies specifically bind to epitopes present in a mammalian serine racemase having an amino acid sequence encoded by polynucleotide molecules comprising the nucleotide sequences shown in SEQ ID NOS: 1, 2, 3, or 9. Typically, at least 6, 8, 10, or 12 contiguous amino acids are required to form an epitope. However, epitopes which involve non-contiguous amino acids may require more, e.g., at least 15, 25, or 50 amino acids.

Epitopes of mammalian serine racemase which are particularly antigenic can be selected, for example, by routine screening of mammalian serine racemase polypeptides for antigenicity or by applying a theoretical method for selecting antigenic regions of the protein, using methods such as those taught in Harlow & Lane (1988), Hopp & Wood, Proc. Natl. Acad. Sci. U.S.A. 78, 3824–28 (1981), Hopp & Wood, Mol. Immunol. 20, 483–89 (1983), and Sutcliffe et al., Science 219, 660–66 (1983).

Any type of antibody known in the art can be generated to bind specifically to mammalian serine racemase epitopes. For example, preparations of polyclonal and monoclonal antibodies can be made using standard methods which are well known in the art. Similarly, single-chain antibodies can also be prepared. Single-chain antibodies which specifically bind to mammalian serine racemase epitopes can be isolated, for example, from single-chain immunoglobulin display libraries, as is known in the art and described, for example, in Hayashi et al., 1995, Gene 160: 129–30. Single-chain antibodies can also be constructed using a DNA amplification method, such as the polymerase chain reaction (PCR), using hybridoma cDNA as a template. Thirion et al., 1996, Eur. J. Cancer Prev. 5: 507–11.

Single-chain antibodies can be mono- or bispecific, and can be bivalent or tetravalent. Construction of tetravalent, bispecific single-chain antibodies is taught, for example, in Coloma and Morrison, 1997, Nat. Biotechnol. 15: 159–63.

Construction of bivalent, bispecific single-chain antibodies is taught inter alia in Mallender and Voss, 1994, *J. Biol. Chem.* 269: 199–206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology. Verhaar et al., 1995, *Int. J. Cancer* 61: 497–501; Nicholls et al., 1993, *J. Immunol. Meth.* 165: 81–91.

For use in therapeutic methods, monoclonal and other antibodies can be "humanized" in order to prevent a patient from mounting an immune response against the antibody. Such antibodies can be sufficiently similar in sequence to human antibodies to be used directly in therapy or may require alteration of a few key residues. Sequence differences between, for example, rodent antibodies and human sequences can be minimized by replacing residues which differ from those in the human sequences, for example, by site directed mutagenesis of individual residues, or by grafting of entire complementarity determining regions. Alternatively, one can produce humanized antibodies using recombinant methods, as described in GB2188638B. Antibodies which specifically bind to mammalian serine racemase epitopes can contain antigen binding sites which are either partially or fully humanized, as disclosed in U.S. Pat. No. 5,565,332.

Other types of antibodies can be constructed and used in methods of the invention. For example, chimeric antibodies can be constructed as disclosed, for example, in WO 93/03151. Binding proteins which are derived from immunoglobulins and which are multivalent and multispecific, such as the "diabodies" described in WO 94/13804, can also be prepared.

Antibodies of the invention can be purified by methods well known in the art. For example, antibodies can be affinity purified by passing the antibodies over a column to which a mammalian serine racemase protein, polypeptide, or fusion protein is bound. The bound antibodies can then be eluted from the column, using a buffer with a high salt concentration.

In one embodiment of the invention, serine racemase is inhibited by administering antibodies which specifically bind to serine racemase to a patient in need of such inhibition. Preparation of such antibodies is described above.

Coding sequences for mammalian serine racemase proteins are shown in SEQ ID NOS: 1, 2, 3, and 9. SEQ ID NO: 1 is the coding sequence for mouse serine racemase. SEQ ID NO: 9 comprises the coding sequence for mouse serine racemase. SEQ ID NOS: 2 and 3 encode the N- and C-termini of human serine racemase, respectively. Full-length cDNA encoding the human enzyme can be obtained using polynucleotide probes selected from SEQ ID NOS: 2, 3, or 9 to screen human cDNA using methods known in the art. Alternatively, human expression libraries can be screened for cDNA clones which express human serine racemase using specific antibodies of the invention.

Isolated and purified mammalian serine racemase polynucleotide molecules according to the invention are subgenomic and contain less than a whole chromosome. Preferably, the polynucleotides are intron-free. Isolated and purified polynucleotide molecules of the invention can be single-or double-stranded and can comprise at least 362, 400, 500, 600, 700, 800, 900, or 1000 contiguous nucleotides selected from SEQ ID NOS: 1 or 9 or can comprise SEQ ID NOS: 1, 2, 3, or 9.

Complements of the nucleotide sequences shown in SEQ ID NOS: 1,2,3, and 9 are contiguous nucleotide sequences which form Watson-Crick base pairs with a contiguous nucleotide sequence of SEQ ID NOS: 1, 2, 3, and 9. Complements of the nucleotide sequences shown in SEQ ID NOS: 1, 2, 3, and 9 are polynucleotides of the invention and can be used, for example, to provide antisense oligonucleotides, primers, and probes. Antisense oligonucleotides, primers, and probes of the invention can consist of at least 11, 12, 15, 20, 25, 30, 50, or 100 contiguous nucleotides which are complementary to the coding sequences shown in SEQ ID NOS: 1, 2, 3, and 9. A complement of the entire coding sequence can also be used.

Degenerate nucleotide sequences which encode amino acid sequences of mammalian serine racemase protein as well as homologous nucleotide sequences which are at least 85%, 90%, 95%, 96%, 97%, 98%, or 99% identical to the nucleotide sequences shown in SEQ ID NOS: 1, 2, 3, and 9, are also polynucleotides of the invention. Percent sequence identity is determined using computer programs which employ the Smith-Waterman algorithm, for example as implemented in the MPSRCH program (Oxford Molecular), using an affine gap search with the following parameters: a gap open penalty of 12 and a gap extension penalty of 1.

Nucleotide sequences which hybridize to the coding sequences shown in SEQ ID NOS: 1, 2, 3, or 9 or their complements with at most 1, 2, 3, 4, 5, 10, 15, 20, 25, 30, or 35% basepair mismatches are also polynucleotides of the invention. For example, using the following wash conditions—2×SSC (0.3 M sodium chloride, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each—homologous polynucleotide sequences can be identified which contain at most about 25–30% basepair mismatches with SEQ ID NOS: 1, 2, 3, or 9. More preferably, homologous nucleic acid strands contain 15–25% basepair mismatches, even more preferably 5–15% basepair mismatches.

Other mammalian serine racemase-encoding polynucleotides can be identified by making suitable probes or primers and screening cDNA expression libraries from other mammals, such as monkey, pig, cow, sheep, goat, or guinea pig. Similarly, serine racemase enzymes from non-mammalian species, such as yeast and *Drosophila*, can be identified by screening cDNA expression libraries from these species using degenerate probes and primers based on the polynucleotide sequences disclosed herein. The $T_m$ of a double-stranded DNA decreases by 1–1.5° C. with every 1% decrease in homology (Bonner et al., *J. Mol. Biol.* 81, 123 (1973). Homologous mammalian or non-mammalian serine racemase polynucleotides can therefore be identified, for example, by hybridizing a putative homologous polynucleotide with a polynucleotide having a nucleotide sequence as shown in SEQ ID NOS: 1, 2, 3, or 9, comparing the melting temperature of the test hybrid with the melting temperature of a hybrid comprising a polynucleotide having SEQ ID NOS: 1, 2, 3, or 9 and a polynucleotide which is perfectly complementary to that sequence, and calculating the number or percent of basepair mismatches within the test hybrid.

Nucleotide sequences which hybridize to the coding sequences shown in SEQ ID NOS: 1, 2, 3, or 9 under stringent hybridization and/or wash conditions are also polynucleotides of the invention. Stringent wash conditions are well known and understood in the art and are disclosed, for example, in Sambrook et al., MOLECULAR CLONING: A LABORATORY MANUAL, 2d ed., 1989, at pages 9.50–9.51.

Typically, stringent hybridization conditions include a combination of temperature and salt concentration that is approximately 12–20° C. below the calculated $T_m$ of the hybrid under study. The $T_m$ of a hybrid between the polynucleotide sequences shown in SEQ ID NOS: 1, 2, 3, and 9 and a polynucleotide sequence which is 85%, 90%, 95%, 96%, 97%, 98%, or 99% identical can be calculated, for example, using the equation of Bolton and McCarthy, *Proc. Natl. Acad. Sci. U.S.A.* 48, 1390 (1962):

$$T_m = 81.5° C. - 16.6(\log_{10}[Na^+]) + 0.41(\% \ G+C) - 0.63(\% \ formamide) - 600/l,$$

where l=the length of the hybrid in basepairs.

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

Polynucleotides of the invention can be isolated and purified free from other nucleotide sequences using standard nucleic acid purification techniques. For example, restriction enzymes and probes can be used to isolate polynucleotide fragments which comprise coding sequences for a mammalian serine racemase. Isolated and purified polynucleotides are in preparations which are free or at least 90% free of other molecules.

Complementary DNA (cDNA) molecules which encode mammalian serine racemase proteins are also polynucleotides of the invention. cDNA molecules can be made using standard molecular biology techniques, with mammalian serine racemase mRNA as a template. cDNA molecules can thereafter be replicated using molecular biology techniques known in the art and disclosed in manuals such as Sambrook et al., 1989. An amplification technique, such as the polymerase chain reaction (PCR), can be used to obtain additional copies of polynucleotides of the invention, using either genomic DNA or cDNA as a template.

Alternatively, synthetic chemistry techniques can be used to synthesize polynucleotide molecules of the invention. The degeneracy of the genetic code allows alternate nucleotide sequences to be synthesized which will encode mammalian serine racemase proteins. All such nucleotide sequences are within the scope of the present invention.

The invention also provides polynucleotide probes which can be used to detect sequences which encode mammalian serine racemase, for example, in hybridization protocols such as Northern or Southern blotting or in situ hybridization. Polynucleotide probes of the invention comprise at least 12, 13, 14, 15, 16, 17, 18, 19, 20, 30, or 40 or more contiguous nucleotides selected from SEQ ID NOS: 1, 2, 3, or 9. Polynucleotide probes of the invention can comprise a detectable label, such as a radioisotopic, fluorescent, enzymatic, or chemiluminescent label.

Using recombinant DNA techniques, a polynucleotide of the present invention can be ligated together with other polynucleotide sequences to form an expression construct. Such expression constructs can be used to express all or a portion of a mammalian serine racemase, such as a mouse, rat, or human serine racemase, in a host cell. An expression construct of the invention comprises a polynucleotide segment encoding the desired amino acid sequence and a promoter which is functional in the particular host cell selected. The skilled artisan can readily select an appropriate promoter from the large number of cell type-specific promoters known and used in the art. The polynucleotide segment is located downstream from the promoter. Transcription of the polynucleotide segment initiates at the promoter. An expression construct can also contain a transcription terminator which is functional in the host cell. The expression construct can be linear or circular and can contain sequences, if desired, for autonomous replication.

The host cell comprising the expression construct can be prokaryotic or eukaryotic. A variety of host cells for use in mammalian, yeast, bacterial, or insect expression systems are available and can be used to express the construct. Suitable mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, baby hamster kidney cells, HL-60, U937, HaK, or Jurkat cells.

Yeast or prokaryotic host cells can also be used to produce mammalian serine racemase. Suitable yeast strains include *Saccharomyces cerevisiae, Schizosaccharomyces pombe, Kluyveromyces* strains, *Candida*, or any yeast strain capable of expressing heterologous proteins. Suitable bacterial strains include *Escherichia coli, Bacillus subtilis, Salmonella typhimurium*, or any bacterial strain capable of expressing heterologous proteins. If the protein is made in yeast or bacteria, it may be necessary to modify it using known chemical or enzymatic methods in order to obtain a functional racemase. Such modification techniques are well known in the art.

Mammalian serine racemase can also be produced in an insect expression system. Materials and methods for baculovirus/insect cell expression systems, for example, are commercially available in kit form from, e.g., Invitrogen, San Diego, Calif., U.S.A. (the MaxBat Registered ™ kit), and such methods are well known in the art, as described in Summers and Smith, Texas Agricultural Experiment Station Bulletin No. 1555 (1987).

According to one embodiment of the invention, mammalian serine racemase is produced by culturing a host cell which comprises an isolated and purified polynucleotide molecule which encodes the racemase under culture conditions suitable to express the recombinant protein. The resulting expressed protein can then be purified from either the culture medium or the host cells using known techniques such as those disclosed in Example 2.

The racemase can be expressed in a form which will facilitate purification. For example, it can be expressed as a fusion protein, such as those of maltose binding protein (MBP), glutathione-S-transferase (GST) or thioredoxin (TRX). Kits for expression and purification of such fusion proteins are commercially available from New England BioLab (Beverly, Mass.), Pharmacia (Piscataway, N.J.) and In Vitrogen, respectively. The protein can also be tagged with an epitope and subsequently purified by using a specific antibody directed to the epitope. One such epitope ("Flag") is commercially available from Kodak (New Haven, Conn.). Monoclonal antibodies which recognize the "Flag" epitope are also commercially available (Kodak Scientific Imaging Systems).

Expression constructs can be introduced into the host cells using any technique known in the art. These techniques include transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and calcium phosphate-mediated transfection.

Viral-based vectors can be used to introduce expression constructs of the invention into host cells. Recombinant retroviruses can be used, as described for example in Mann et al., *Cell* 33: 153, 1983, Cane and Mulligan, *Proc. Natl. Acad. Sci. USA* 81: 6349, 1984, and Miller et al., *Human Gene Therapy* 1: 5–14, 1990, U.S. Pat. Nos. 4,405,712, 4,861,719, and 4,980,289, and PCT Application Nos. WO 89/02,468, WO 89/05,349, and WO 90/02,806. Recombinant adenoviral vectors can also be prepared and used, given the disclosure provided herein (see Berkner, *Biotechniques* 6: 616, 1988, and Rosenfeld et al., *Science* 252: 431, 1991, WO 93/07283, WO 93/06223, and WO 93/07282). Adeno-associated viral vectors can also be used to deliver polynucleotides of the invention to host cells. The use of adeno-associated viral vectors in vitro is described in Chatterjee et al., *Science* 258: 1485–1488 (1992), Walsh et al., *Proc. Natl. Acad. Sci.* 89: 7257–7261 (1992), Walsh et al., *J. Clin. Invest.* 94: 1440–1448 (1994), Flotte et al., *J. Biol. Chem.* 268: 3781–3790(1993), Ponnazhagan et al., *J. Exp. Med.* 179: 733–738(1994), or Miller et al., *Proc. Natl. Acad. Sci.* 91: 10183–10187(1994), Einerhand et al., *Gene Ther.* 2: 336–343 (1995), Luo et al., *Exp. Hematol.* 23: 1261–1267 (1995), and Zhou et al., *Gene Therapy* 3: 223–229 (1996). In vivo use of these vehicles is described in Flotte et al., *Proc. Natl. Acad. Sci* 90: 10613–10617 (1993), and Kaplitt et al., *Nature Genet.* 8: 148–153 (1994).

Other viruses which can be used to construct vectors include herpes simplex virus (Kit et al., *Adv. Exp. Med. Biol.* 215: 219, 1989) (ATCC VR-977; ATCC VR-260); *Nature* 277: 108, 1979), human immunodeficiency virus (EPO 386,882, Buchschacher et al., *J. Vir.* 66: 2731, 1992), and measles virus (EPO 440,219) (ATCC VR-24); A (ATCC VR-67; ATCC VR-1247). Any suitable vector known in the art can be used to introduce polynucleotides or expression constructs of the invention into host cells.

Endogenous D-serine is required for physiologic NMDA neurotransmission. Treatment of brain slices or cultures with D-amino acid oxidase, under conditions in which D-serine is completely degraded, greatly reduces NMDA transmission, whether measured neurophysiologically or by measuring stimulation of nitric oxide synthase activity or levels of cyclic GMP. Drugs which inhibit mammalian serine racemase can be used to treat conditions or diseases in which NMDA overexcitation is found. In particular, such conditions include those for which NMDA receptor antagonists have displayed efficacy.

For example, activation of NMDA receptors is an important pathologic event in stroke and several neurodegenerative diseases. Inhibitors of serine racemase can be used to decrease D-serine levels in the brain and consequently decrease the activation of NMDA receptors. Identification of agents which inhibit serine racemase is therefore important in the treatment of any disease that includes acute or chronic neuronal death or dysfunction mediated by overactivation of NMDA receptors, such as stroke, epilepsy, and chronic neurodegenerative diseases such as Parkinson's disease, Huntington's disease, motor neuron diseases, and Alzheimer's disease.

In one embodiment of the invention serine racemase is inhibited using an antisense oligonucleotide. The sequence of the antisense oligonucleotide is complementary to at least a portion of a coding sequence as shown in SEQ ID NOS: 1, 2, 3, or 9. Preferably, the antisense oligonucleotide is at least six nucleotides in length, but can be at least 8, 11, 12, 15, 20, 25, 30, 35, 40, 45, or 50 nucleotides long. Longer sequences can also be used.

Antisense oligonucleotides can be composed of deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such as alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, 1994, *Meth. Mol. Biol.* 20: 1–8; Sonveaux, 1994, *Meth. Mol. Biol.* 26: 1–72; Uhlmann et al., 1990, *Chem. Rev.* 90: 543–583.

Although desirable, precise complementarity is not required for successful duplex formation between an antisense molecule and the complementary coding sequence of a polynucleotide which encodes a mammalian serine racemase. Antisense molecules which comprise, for example, 2, 3, 4, or 5 or more stretches of contiguous nucleotides which are precisely complementary to a mammalian serine racemase coding sequence, each separated by a stretch of contiguous nucleotides which are not complementary to adjacent coding sequences, can provide sufficient targeting specificity for mammalian serine racemase mRNA. Preferably, each stretch of contiguous nucleotides is at least 4, 5, 6, 7, or 8 or more nucleotides in length. Non- complementary intervening sequences are preferably 1, 2, 3, or 4 nucleotides in length. One skilled in the art can easily use the calculated melting point of an antisense-sense pair to determine the degree of mismatching which will be tolerated between a particular antisense oligonucleotide and a particular coding sequence.

Antisense oligonucleotides can be modified without affecting their ability to hybridize to a mammalian serine racemase coding sequence. These modifications can be internal or at one or both ends of the antisense oligonucleotide. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3',5'-substituted oligonucleotide in which the 3' hydroxyl group or the 5' phosphate group are substituted, can also be used in a modified antisense oligonucleotide. These modified oligonucleotides can be prepared by methods well known in the art. Agrawal et al., *Trends Biotechnol.* 10: 152–158, 1992; Uhlmann et al., *Chem. Rev.* 90: 543–584, 1990; Uhlmann et al., *Tetrahedron. Lett.* 215: 3539–3542, 1987.

Therapeutic compositions of the invention can also comprise a pharmaceutically acceptable carrier. Pharmaceutically acceptable carriers are well known to those in the art. Such carriers include, but are not limited to, large, slowly metabolized macromolecules, such as proteins, polysaccharides, polylactic acids, polyglycolic acids, polymeric amino acids, amino acid copolymers, and inactive virus particles. Pharmaceutically acceptable salts can also be used, for example, mineral salts such as hydrochlorides, hydrobromides, phosphates, or sulfates, as well as the salts of organic acids such as acetates, proprionates, malonates, or benzoates. Therapeutic compositions can also contain liquids, such as water, saline, glycerol, and ethanol, as well as substances such as wetting agents, emulsifying agents, or pH buffering agents. Liposomes, such as those described in U.S. Pat. No. 5,422,120, WO 95/13796, WO 91/14445, or EP 524,968 B1, can also be used as a carrier for a therapeutic composition. Typically, a therapeutic composition of the invention is prepared as an injectable, either as a liquid solution or suspension; however, solid forms suitable for solution in, or suspension in, liquid vehicles prior to injection can also be prepared.

Administration of antisense oligonucleotides or antibodies of the invention can include local or systemic administration, including injection, oral administration, particle gun, or catheterized administration. Various methods can be used to administer a therapeutic composition directly to a specific site in the body. For example, receptor-mediated targeted delivery can be used to deliver therapeutic compositions containing antisense oligonucleotides or antibodies to specific tissues. Receptor-mediated delivery techniques are described, for example, in Findeis et al. (1993) *Trends in Biotechnol.* 11, 202–05; Chiou et al. (1994), GENE THERAPEUTICS: METHODS AND APPLICATIONS OF DIRECT GENE TRANSFER (J. A. Wolff, ed.); Wu & Wu (1988), *J. Biol. Chem.* 263, 621–24; Wu et al. (1994), *J. Biol. Chem.* 269, 542–46; Zenke et al. (1990), *Proc. Natl. Acad. Sci. U.S.A.* 87, 3655–59; Wu et al. (1991), *J. Biol. Chem.* 266, 338–42.

If the composition contains antibodies, effective dosages of the composition are in the range of about 5 µg to about 50 µg/kg of patient body weight, about 50 µg to about 5 mg/kg, about 100 µg to about 500 µg/kg of patient body weight, and about 200 to about 250 µg/kg. Therapeutic compositions containing antisense oligonucleotides can be administered in a range of about 100 µg to about 200 µg, about 500 µg to about 50 µg, about 1 µg to about 2 mg, about 5 µg to about 500 µg, or about 20 µg to about 100 µg. Factors such as method of action and efficacy of transformation and expression are considerations that will effect the dosage required for ultimate efficacy of therapeutic compositions of the invention. Where greater expression is desired over a larger area of tissue, larger amounts of therapeutic compositions or the same amounts readministered in successive administrations can be used to effect a positive therapeutic outcome. In all cases, routine experimentation in clinical trials will determine specific ranges for optimal therapeutic effect.

The invention also provides a method of screening test compounds to identify candidate therapeutic agents which modulate the activity of mammalian serine racemase. Modulators can either increase or decrease the specific activity of mammalian serine racemase. A test compound can be a pharmacologic agent already known in the art or can be a compound previously unknown to have any pharmacological activity. The compound can be naturally occurring or designed in the laboratory. It can be isolated from microorganisms, animals, or plants, and can be produced recombinantly, or synthesized by chemical methods known in the art.

A test compound is contacted with a mammalian serine racemase, such as a rat, mouse, or human serine racemase. The activity of the serine racemase can be assayed as described in Example 2. Any other suitable assay for serine racemase activity can also be used.

A test compound is identified as a candidate therapeutic agent if it modulates the activity of the mammalian serine racemase. Preferably the activity of the mammalian serine racemase is increased or decreased by at least 50%, 60%, 70%, or 80%. Most preferably, activity is increased or decreased by 90%, 95%, 99%, or 100%.

The complete contents of all references cited in this disclosure are incorporated herein by reference. The following examples are provided for exemplification purposes only and are not intended to limit the scope of the invention which has been described in broad terms above.

EXAMPLES

The following materials were used in the examples below.

Amino acids, aminooxyacetic acid (AOAA), catalase, oxidized glutathione, hydroxylamine, leupeptin, luminol (sodium salt), pepstatin, phenylmethylsulfonyl fluoride, pyridoxal 5'-phosphate (PLP), o-phthaldialdehyde (OPA), L-homocysteic acid, and Tris were obtained from Sigma (St. Louis). D-amino acid oxidase from pig kidney (EC 1.4.3.3), dithiothreitol (DTT), and horseradish peroxidase were obtained from Boehringer Mannheim. Ammonium sulfate and $KH_2PO_4$ were purchased from J. T. Baker. Butyl sepharose 4 fast flow, Q-sepharose, mono Q HR 5/5 were obtained from Pharmacia Macro-prep ceramic hydroxyapatite type I (20 µM) was purchased from Bio-Rad. N-tert-butyloxycarbonyl-L-cysteine (L-Boc-cys) was obtained from Novabiochem. Other reagents were of analytical grade.

Example 1

This example demonstrates purification of mammalian serine racemase.

Sixty brains from 10–14 day old Sprague-Dawley rats were homogenized using a Polytron in 5 volumes of ice-cold buffer A (10 mM KPi, pH 7.2, 50 mM KCl, 1 mM EDTA, 2 mM DTT, 15 µM PLP, 0.2 mM freshly prepared phenylmethylsulfonyl fluoride, 1 µg/ml leupeptin, 1 µg/ml pepstatin). All subsequent steps were performed at 4° C. The homogenate was centrifuged at 40,000×g for 20 minutes, and the supernatant was brought to 45% ammonium sulfate saturation under continuous stirring. After a 40 minutes precipitation, the solution was centrifuged at 20,000×g for 20 minutes. The pellet was resuspended in 20% ammonium sulfate in buffer A. The suspension was left on ice for 1 hour and then centrifuged at 20,000×g for 20 minutes to remove insoluble aggregates.

The supernatant was loaded at 3 ml/minute onto a 70 ml butyl-sepharose column pre-equilibrated with 20% ammonium sulfate in buffer A. The column was washed with 210 ml of 10% ammonium sulfate, and the active fraction was eluted with 5% ammonium sulfate in buffer A. The eluted material was concentrated by precipitation with 50% ammonium sulfate and centrifugation at 20,000×g for 20 min. The pellet was resuspended in 6–8 ml buffer A and dialyzed overnight against 4 liters of buffer B (10 mM KPi, pH 7.2, 50 mM KCl, 1 mM EDTA, 2 mM DTT, 15 µM PLP). After dialysis, the suspension was centrifuged at 20,000×g for 20 minutes to remove insoluble aggregates, and the supernatant was loaded at 0.5 ml/ml onto a 3 ml Q-sepharose column.

After washing with 10 ml loading buffer, the protein was eluted with 250 mM NaCl in buffer B. The eluted material was concentrated with centriprep 30 (Amicon, Lexington, Mass.) and diluted in buffer B without KCl to decrease the salt concentration to 50 mM. Then, the suspension was loaded at 0.5 ml/minutes onto mono Q column. The column was washed with buffer B containing 150 mM KCl, and the protein was eluted with a linear gradient of KCl in the range of 158 to 188 mM Kcl.

The active fractions were pooled, concentrated with centriplus 30 (Amicon, Lexington, Mass.) and diluted in buffer B without EDTA and KPi. The procedure was repeated once to decrease the EDTA and KPi concentrations to 20 µM and 0.75 mM, respectively. To this suspension, $CaCl_2$ was added (300 µM final concentration) to improve the protein binding to hydroxyapatite. The protein was applied at 0.1 ml/minutes to a 1 ml hydroxyapatite column, and eluted with a linear gradient of 0.75 to 400 mM KPi in buffer containing 50 mM KCl, 2 mM DTT and 15 µM PLP. The purified protein was typically eluted in the range of 0.75 to 30 mM Kpi.

Figure 1:
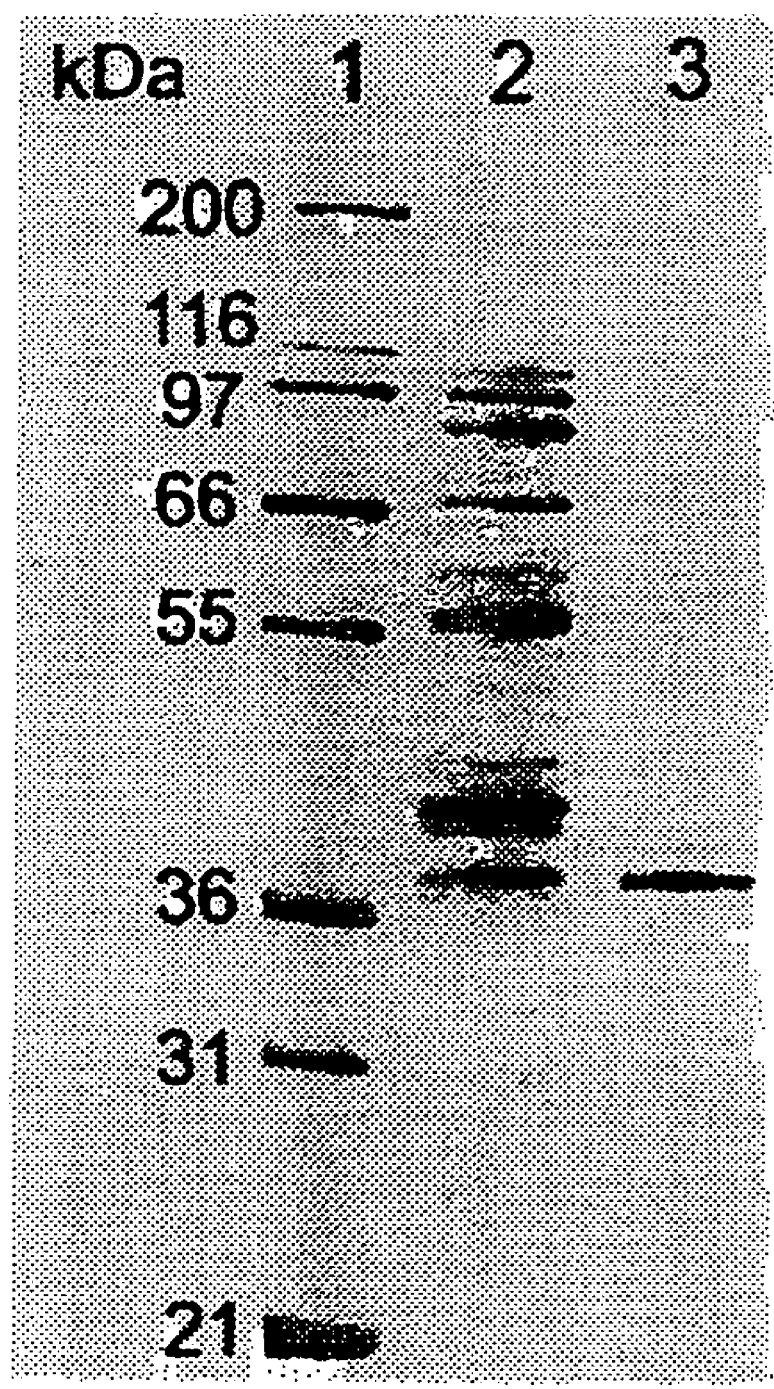
FIG. 1. SDS/PAGE analysis of purified serine racemase. A 12% polyacrylamide gel was stained with Coomassie blue. Lane 1, molecular weight markers: myosin (200 kDa); β-galactosidase (116.7 kDa); phosphorylase b (97.4 kDa); bovine serum albumin (66.3 kDa); glutamic dehydrogenase (55.4 kDa); lactate dehydrogenase (36.5 kDa); carbonic anhydrase (31 kDa); trypsin inhibitor (21.5 kDa). Lane 2, mono Q column eluate containing 1 $\mu$g protein. Lane 3, Hydroxyapatite column eluate containing 0.5 $\mu$g of purified protein. Silver staining of the purified preparation showed no additional bands.

For most applications the purified protein was further concentrated using centriplus 30. Protein concentration was determined with Coomassie plus protein assay reagent (Pierce). Enzyme-bound PLP was determined at room temperature by recording the absorbance of the purified protein in the range of 500 to 280 nm using a Lambda Bio spectrophotometer (Perkin Elmer). SDS gel electrophoresis revealed a single band for the purified protein of about 37 kDa (FIG. 1).

We have therefore purified the enzyme to homogeneity utilizing sequentially ammonium sulfate fractionation, butyl-sepharose, Q-sepharose, mono-Q, and hydroxyapatite chromatography steps (Table 1). The overall purification from the ammonium sulfate fraction is 12,500. Enzyme activity is obtained in 30% yield. Interestingly, there is an apparent increase in yield following the Q-sepharose step, suggesting the removal of an inhibitor.

Serine racemase is a relatively small soluble protein of 37 kDa. Its absorption spectrum indicates that no minor, undetected protein could account for enzyme activity. The magnitude and ratios of absorption at 280, 340, and 420 nm closely resemble values for known PLP enzymes (20, 23,24). This could only be possible if essentially all the protein is the PLP-requiring racemase.

The enzyme is stable with no loss of activity when stored for 4 days at 4° C. Only modest loss of activity occurs after two cycles of freezing and thawing. The enzyme appears to be soluble with no activity detected in a membrane preparation. Enzyme activity displays a sharp pH optimum in the alkaline range, with optimal activity at pH 8–9 being about 10 times higher than at pH 7 (FIG. 2). Enzyme activity is maximal at 37° C., and is abolished by boiling.

Example 2

This example demonstrates an assay of serine racemase activity.

D-serine formation was monitored by a chemiluminescent assay that specifically detects D-serine. Racemase activity was performed in the presence of 50 mM Tris-HCl (pH 8.0), 18 µl enzyme extract, 1 mM EDTA, 2 mM DTT, 15 µM pyridoxal 5'-phosphate (PLP), and 20 mM L-serine. After 0.5 to 8 hours incubation at 37° C., the reaction was terminated by the addition of trichloroacetic acid (TCA) to a final concentration of 5%. Blanks employed boiled enzyme extract. The precipitated protein was removed by centrifugation, and the supernatant was extracted 2 times with 1 ml of water-saturated diethyl ether to remove TCA. D-serine concentration was determined by incubation of the samples with D-amino acid oxidase, which specifically degrades D-amino acids, generating an α-keto acid, $NH_3$ and hydrogen peroxide (16).

The generation of hydrogen peroxide was quantitated by the use of peroxidase and luminol, which emits light. A 10 µl sample aliquot was added to 100 µl of medium containing 100 mM Tris-HCl (pH 8.8), 10 U/ml peroxidase, and 8 µM luminol. After a 10 to 20 minute delay required to decrease the nonspecific luminol luminescence, 10 µl of D-amino acid oxidase (75 U/ml) were added, and the tubes were gently mixed with a pipette tip. Maximum luminescence was recorded after 10 to 15 minutes at room temperature using a Monolight 2010 luminometer (Analytical Luminescence Laboratory). The amount of D-serine in each sample was calculated by comparison with standard curves. The measurements were reliable in the range of 50 to 2000 pmol D-serine per sample. Addition of mM concentrations of L-serine did not alter the values measured for D-serine. Alternatively, amino acid enantiomers were separated by high performance liquid chromatography (HPLC) using a carbon 18 reverse phase column (RP18 Spheri-5, 22 cm×4.6 mm, Perkin Elmer) with fluorimetric detection after derivatization with L-Boc-cys and OPA, as described (17). The results obtained with chemiluminescent assay were identical to those obtained using HPLC.

The presence of trace amounts of D-serine in the commercial L-serine reagent generates high blank values. Thus, the stock solution of L-serine (100 mM) was routinely pre-treated for 3 days with 30 units of D-amino acid oxidase and 500 units of catalase to remove any D-serine contaminant. The enzymes were precipitated by the addition of 5% TCA. After removal of TCA by extraction with diethyl ether, the L-serine solution was neutralized with NaOH and could be used without further purification, being virtually free of any D-serine contaminant. The same purification procedure was applied for L-alanine and L-threonine.

Example 3

Figure 3:
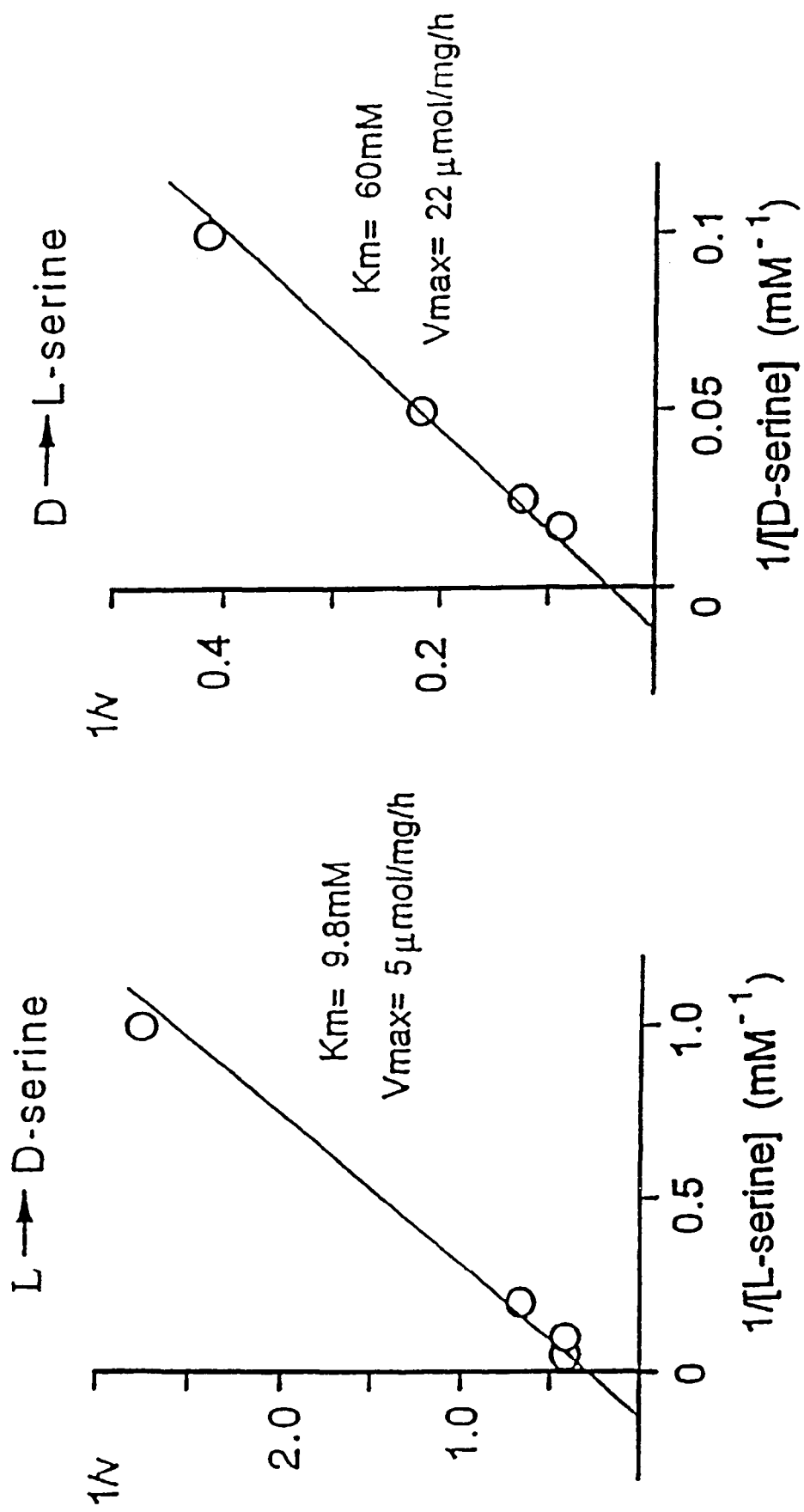
FIG. 3. Kinetic parameters of racemization reaction. Initial rate of racemase activity was measured at 37° C. in a medium containing 50 mM Tris-HCl (pH 8.0), 35 µg/ml purified enzyme, 1 mM EDTA, 2 mM DTT, 15 µM pyridoxal 5'-phosphate, and different concentrations of either L- or D-serine. The reaction was stopped after 2 hours, when less than 10% of the substrate was consumed. Values for $K_m$ and $V_{max}$ were calculated using the Michaelis-Menten equation. The values are representative of three experiments with different enzyme preparations.

This example demonstrates that mammalian serine racemase activity obeys Michaelis-Menten kinetics (FIG. 3).

Monitoring the conversion of L to D-serine, the $K_m$ is about 10 mM with a $V_{max}$ of 5 µmol/mg/h. The enzyme can also convert D- to L-serine but with lesser affinity: the $K_m$ in this direction is 60 mM, though the $V_{max}$ is higher, 22 µmol/mg/h.

Example 4

This example demonstrates that mammalian serine racemase requires pyridoxal 5'-phosphate (PLP).

Dialysis for 16 hours against 1,000 volumes of the purification buffer without PLP abolishes enzyme activity, which can be restored by the addition of PLP. Aminooxyacetic acid (AOAA) and hydroxylamine, which inactivate PLP, inhibit enzyme activity (FIG. 4). Examination of the absorption spectrum of the enzyme confirms the importance of PLP. Thus, the normal enzyme preparation displays absorption peaks at 420 nm and 340 nm, characteristic of PLP-dependent enzymes. The peak at 420 nm, corresponding to a Schiff's base complex of PLP with an active site lysine, is abolished by treatment with AOAA (FIG. 5).

Sulfhydryl groups seem to be important for enzyme activity, as oxidized glutathione markedly reduces enzyme activity (FIG. 4). We wondered whether conversion of L to D-serine might be a by-product of a different enzyme activity with non-enzymatic racemization giving rise to D-serine. Accordingly, we monitored by HPLC levels of L and D-serine at different incubation times (Table 2). Increases in formation of D-serine are paralleled by stoichiometric decreases in levels of L-serine, making it unlikely that L-serine is converted to any other compound by the enzyme.

Additionally, we examined the purified enzyme for the presence of other enzyme activities which might indirectly contribute to D-serine formation. We found no evidence for serine: pyruvate aminotransferase activity, as L-serine levels were not altered in the presence of pyruvate. We did not observe serine hydroxymethyltransferase activity inasmuch as we fail to detect the formation of glycine after extensive incubation of the enzyme with L-serine. There is no evidence for serine dehydratase activity which would be associated with a marked decrease in L-serine levels. Serine racemase is highly selective for L-serine (Table 3). The enzyme displays about 1.5% as much activity toward L-alanine as for L-serine, while no activity is demonstrated with L-threonine or L-aspartate.

Example 5

This example demonstrates cloning of mammalian serine racemase.

Purified rat serine racemase was submitted to internal peptide sequencing and the following amino acid peptides were identified:
LLIEPTAGVGLAAVLSQTVSPEVK (SEQ ID NO: 6)
HLNIQDSVHLTPVLTSSILNQIAGR (SEQ ID NO: 7).

Blast search using the blastp program did not reveal any protein with significant homology to the peptides.

We performed a blast search using the tblastn program against the EST database and found several independent ESTs sequences with unknown function that covered the N-terminal and the C-terminal regions of the protein (Accession numbers AA170919 (mouse), AI173393, AA034539, W89934, AA509764, AA833469). To obtain full length cDNA clones, we designed the following PCR primers based on the EST sequences we found in the database, containing restriction sites for SalI and NotI: 5' ACGCGTCGACCACCATGTGTGCTCAGTACTGC 3' (SEQ ID NO: 4) and 5' ATAAGAATGCGGCCGCTTAAACAGAAACCGTCTG 3' (SEQ ID NO: 5).

Full length cDNA encoding mouse serine racemase was cloned by PCR from mouse brain cDNA obtained by reverse transcription of poly A RNA purchased from Clontech (Palo Alto, Calif.). The coding sequence is shown in SEQ ID NO: 1. The corresponding deduced amino acid sequence is shown in SEQ ID NO: 5.

Example 6

This example demonstrates expression of mammalian serine racemase.

Serine racemase was cloned on mammalian expression vector PRK5 in SalI/NotI. HEK 293 cells were transfected with the fill length racemase using the calcium chloride method. The cell were cultured Dulbecco's modified Eagles Medium supplemented with penicillin and streptomycin as described in Sawa et al., *Proc. Natl. Acad. Sci. U.S.A.* 94, 11669–74 (1997). The medium was supplemented with 10 mM L-serine for measurement of D-serine production. Culture medium and cell pellets were analyzed 48 hours after transfection for the presence of D-serine as described above.

Figure 6:
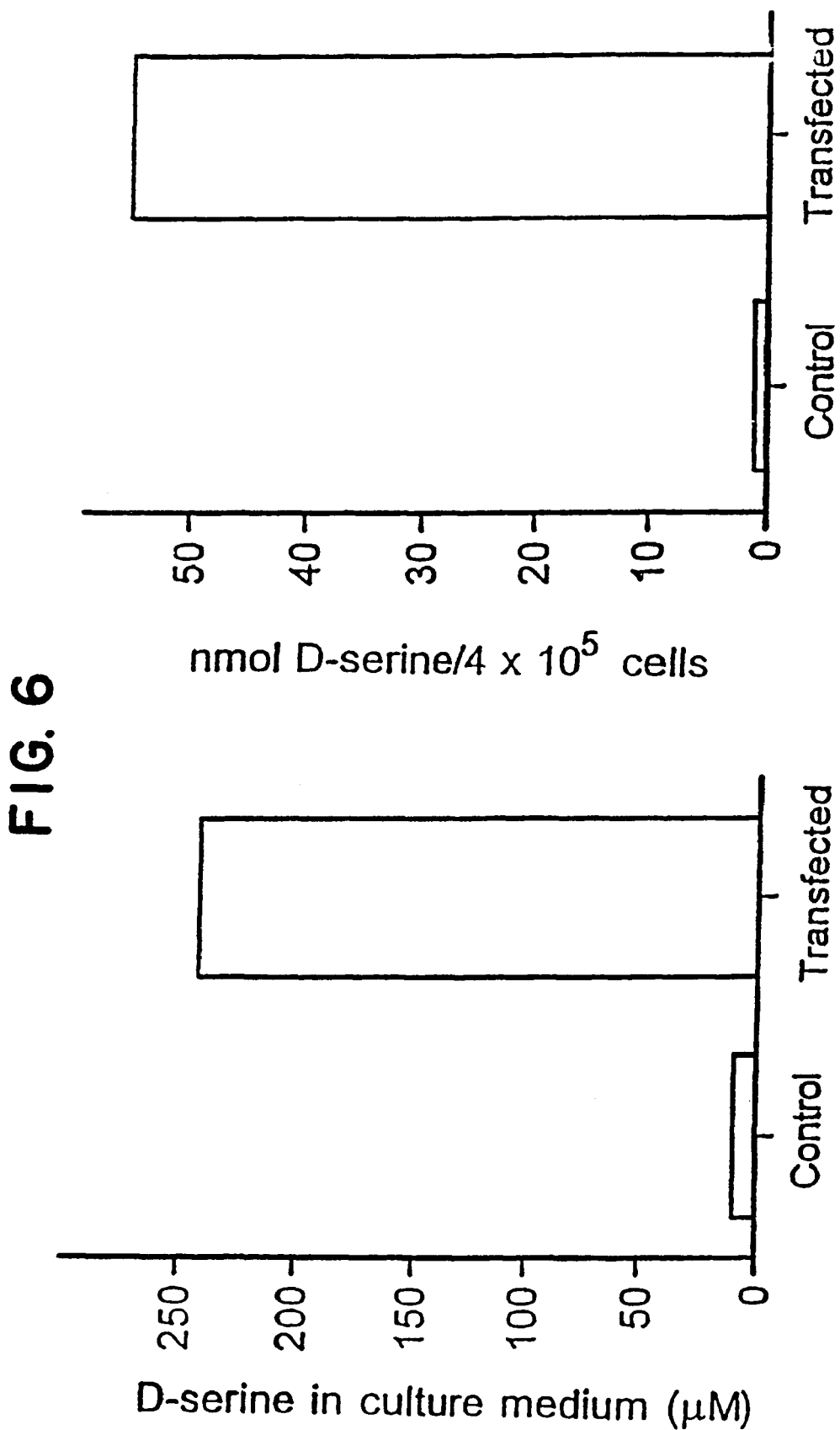
FIG. 6. Production of D-serine in culture medium of cells transfected with cDNA encoding full-length serine racemase (left) and in the transfected cells (right).

Transfection of cells with cDNA encoding full-length serine racemase promoted a highly significant increase in D-serine concentration both in the medium and in the cell pellets (FIG. 6). Cells transfected with vector alone showed only traces of D-serine.

Example 7

This example demonstrates the deduction of the coding sequence of human serine racemase.

Based on the mouse sequence, we searched the public database and found several human ESTS of unknown function with high homology to the mouse sequence. We generated a partial sequence of the human serine racemase gene by alignment of 11 of the ESTS. The partial sequence comprises the following contigs:

Contig 1 (SEQ ID NO: 2)

GGCGCGGCGCCGATGAGCTGAGAACCATGTGTGCTCAGTATTGCATCT
CCTTTGCTGATGTTGAAAAAGCTCATATCAACATTCGAGATTCTATCCA
CCTCACACCAGTGCTAACAAGCTCCATTTTGAATCAACTAACAGGGCGC
AATCTTTTCTTCAAATGTGAACTCTTCCAGAAAACAGGATCTTTTAAGA
TTCGTGGTGCTCTCAATGCCGTCAGAAGCTTGGTTCCTGATGCTTTAGA
AAGGAAGCCGAAAGCTGTTGTTACTCACAGCAGTGGAAACCATGGCCA
GGCTCTCACCTATGCTGCCAAATTGGAAGGAATTCCTGCTTATATTGTG
GTGCCCCAGACAGCTCCAGACTGTAAAAAACTTGCAATACAAGCCTAC
GGAGCGTCAATTGTATACTGTGAACCTAGTGATGAAGTCCAGAGAAAA
TGTTGCAAAAAGGAGTTACAGAAGAAACAGAAGGCATCATGGTACATC
CCAACCAGGAACCTGCAGTGATAGCTGGACAAGGGACAATTGCCCTGG
AAGTGCTGAACCAGGTTCCTTTGGTGGATCCACTGGTGGNCCCTGTAGG
TGGAAGGAGGAATGCTTGCCGGGAAT

Contig 2 (SEQ ID NO: 3)

CTGATGCCCAATCTTTATCCTCCAGAAACCATAGCAGATGGTGTCAAA
TCCAGCATTGGCTTGAANCACCTGGCCTATTATCAGGGACCTTGTGGATG
ATATCTTCACTGTCACAGAGGATGAAATTAAGTGTGCAACCCAGCTGGTG
TGGGAGAGGATGAAACTACTCATTGAACCTACAGCTGGTGTTGGAGTGGC
TGCTGTGCTGTCTCAACATTTTCAAACTGTTTCCCCAGAAGTAAAGAACA
TTTGTATTGTGCTCAGTGGTGGAAATGTAGACTTAACCTCCTCCATAACT
TGGGTGAAGCAGGCTGAAAGGCCAGCTTCTTATCAGTCTGTTTCTGTTTA
ATTTACAGAAAAGGAAATGGTGGGAATTCAGTGTCTTTAGATACTGAAGA
CATTTTGTTTCCTAGTATTGTCAACTCTTAGTTATCAGATTCTTAATGGA
GAGTGGCTATTTCATTAAGGTTTAATAGTTTTTTTTGGACTAAGTAGTGG
AAAAACTTTTA

Contig 1 represents the N-terminal of human serine racemase and Contig 2 represents the C-terminal as analyzed by standard DNA alignment program.

TABLE 1

Purification of serine racemase.

| Fraction | Protein (mg) | Specific activity (μmol L-ser/ mg/h) | Fold purification | Total activity | Yield (%) |
|---|---|---|---|---|---|
| Homogenate | 4744 | N.D.[a] | | | |
| (NH₄)₂SO₄ fractionation | 624 | 0.0004 | 1 | 0.249 | 100 |

TABLE 1-continued

Purification of serine racemase.

| Fraction | Protein (mg) | Specific activity (μmol L-ser/ mg/h) | Fold purification | Total activity | Yield (%) |
|---|---|---|---|---|---|
| Butyl-sepharose | 34 | 0.003 | 7.5 | 0.102 | 41 |
| Q-sepharose | 6.6 | 0.029 | 73 | 0.191 | 77 |
| Mono-Q | 0.22 | 0.833 | 2082 | 0.183 | 73 |
| Hydroxyapatite | 0.015 | 5.0 | 12500 | 0.075 | 30 |

Enzyme was purified and fractions were assayed as described. Data represent a typical purification, which was repeated six times with similar results.
[a] Not detected

TABLE 2

Racemization of L-serine

| Time | [L-serine] (mM) | [D-sertne] (mM) |
|---|---|---|
| 0 | 4.00 | 0.0007 |
| 0.5 h | 3.96 | 0.042 |
| 1 h | 3.93 | 0.101 |
| 4 h | 3.65 | 0.342 |

Racemase activity was assayed at 37° C. in a medium containing 50 mM Tris-HCl (pH 8.0). 4 mM L-serine. 40 μg/ml purified enzyme, 1 mM EDTA, 2 mM DTT and 15 μM pyridoxal 5'-phosphate. Samples were analyzed for amino acids enantiomers by HPLC as described.

TABLE 3

Substrate specificity of serine racemase

| Amino acid | Specific activity (μmol/mg/h) | % control |
|---|---|---|
| L-serine | 4.8 | 100 |
| L-alanine | 0.012 | 1.5 |
| L-threonine | 0 | |
| L-aspartate | 0 | 0 |

Racemase activity was assayed at 37° C. in a medium containing 50 mM Tris-HCl (pH 8.0). 20 mM L-amino acids. 40–100 μg/ml purified enzyme, 1 mM EDTA, 2 mM DTT and 15 μM pyridoxal 5'-phosphate. After 8 h, the reaction was terminated by the addition of 5% TCA, and samples were analyzed by HPLC as described. The data represent a typical experiment which was replicated three times using different preparations with similar results.

REFERENCES

1. Corrigan, J. J. (1969) Science 164, 142–149.
2. Corrigan, J. J., and Srinivasan, N. G. (1966) Biochemistry 5, 1185–1190.
3. Nagata, Y., Konno, R., Yasumura, Y. & Akino, T. (1989) Biochem. J. 257, 291–292.
4. Hashimoto, A., Nishikawa, T., Hayashi, T., Fujii, N., Harada, K., Oka, T. & Takahashi, K. (1992) FEBS Lett 296, 33–36.
5. Hashimoto, A, Kumashiro, S., Nishikawa, T., Oka, T., Takahashi, K., Mito, T., Takashima, S., Doi, N., Mizutani, Y., Yamazaki, T., Kaneko, T. & Ootomo, E. (1993) J. Neurochem. 61, 783–786.
6. Nagata, Y., Horiike, K. & Maeda, T. (1994) Brain Res. 634, 291–295.
7. Dunlop, D. S., Neidle, A., McHale, D., Dunlop, D. M. & Lajtha, A. (1986) Biochem. Biophys. Res. Commun. 141, 27–32.
8. Hashimoto, A., Oka, T. & Nishikawa, T. (1995) Eur. J. Neurosci. 7, 1657–1663.
9. Schell, M. J., Cooper, O. B. & Snyder, S. H. (1995) Proc. Natl. Acad. Sci. U.S.A 94, 2013–2018.
10. Schell, M. J., Molliver, M. E. & Snyder, S. H. (1995) Proc. Natl. Acad. Sci. U.S.A. 92, 3948–3952.
11. Schell, M. J., Brady Jr, R. O., Molliver, M. E., & Snyder, S. H. (1997) J. Neurosci. 17, 1604–1615.
12. Johnson, J. W. & Ascher, P. (1987) Nature 325, 529–531.
13. Kleckner, N. W. & Dingledine, R. (1988) Science 241, 835–837.
14. Matsui, T., Sekiguchi, M., Hashimoto, A. Tomita, U., Nishikawa, T., and Wada, K. (1995) J. Neurochem. 65, 454–458.
15. Dunlop, D. S. & Neidle, A. (1997) Biochem. Biophys. Res. Commun. 235, 26–30.
16. Scannone, H., Wellner, D., & Novogrodsky, A. (1964) Biochemistry 11, 1742–1745.
17. Hashimoto, A., Nishikawa, T., Oka, T., Takahashi, K., and Hayashi, T. (1992) J. Chromatogr. 582, 41–48.
18. Uo, T., Yoshimura, T., Shimizu, S. & Esaki, N. (1998) Biochem. Biophys. Res. Commun. 246, 31–34.
19. Wood, W. A. & Gunsalus, I. C. (1951) J. Biol. Chem. 190, 403–416.
20. Yorifuji. T., Misono, H. & Soda, K. (1971) J. Biol. Chem. 246, 5093–5101.
21. Svensson, M. L. & Gatenbeck, S. (1981) Arch. Microbiol 129, 213–215.
22. Olivard, J., Metzler, D. E. & Snell, E. E. (1952) J. Biol. Chem. 191, 669–674.
23. Manohar, R., Apu Rao, A. G. & Appaji Rao, N. (1984) Biochemistry 23, 4116–4122.
24. Ishikawa, K., Kaneko, E. & Ichiyama, A. (1996) J. Biochem. 119, 970–978.

What is claimed is:

1. A method to screen compounds to identify candidate therapeutic agents comprising the steps of:
   contacting a test compound with a serine racemase comprising the amino acid sequence shown in SEQ ID NO:10 or SEQ ID NO:8;
   assaying activity of the serine racemase; and
   identifying a test compound as a candidate therapeutic agent if it modulates the activity of the serine racemase.

2. The method of claim 1 wherein the candidate therapeutic agent inhibits the activity of the serine racemase.

3. The method of claim 1 wherein the candidate therapeutic agent increases the activity of the serine racemase.

4. A method to screen compounds to identify candidate therapeutic agents comprising the steps of:
   contacting a test compound with a preparation of isolated serine racemase which comprises an amino acid sequence which is at least 95% identical to SEQ ID:8 or SEQ ID NO:10 and comprises a pyridoxal 5' phosphate binding region consisting of amino acids 47–60 of SEQ ID NO:8 or SEQ ID NO:10;
   assaying activity of the serine racemase; and
   identifying a test compound as a candidate therapeutic agent if it modulates the activity of the serine racemase.

5. The method of claim 4 wherein the candidate therapeutic agent inhibits the activity of the serine racemase.

6. The method of claim 4 wherein the candidate therapeutic agent increases the activity of the serine racemase.

7. The method of claim 1 wherein the serine racemase comprises the amino acid sequence shown in SEQ ID NO:8.

8. The method of claim 1 wherein the serine racemase comprises the amino acid sequence shown in SEQ ID NO:10.

9. The method of claim 4 wherein the amino acid sequence is at least 95% identical to SEQ ID NO:8.

10. The method of claim 4 wherein the amino acid sequence is at least 95% identical to SEQ ID NO: 10.

11. The method of claim 4 wherein the amino acid sequence is at least 96% identical to SEQ ID NO:8.

12. The method of claim 4 wherein the amino acid sequence is at least 96% identical to SEQ ID NO:10.

13. The method of claim 4 wherein the amino acid sequence is at least 97% identical to SEQ ID NO:8.

14. The method of claim 4 wherein the amino acid sequence is at least 97% identical to SEQ ID NO:10.

15. The method of claim 4 wherein the amino acid sequence is at least 98% identical to SEQ ID NO:8.

16. The method of claim 4 wherein the amino acid sequence is at least 98% identical to SEQ ID NO:10.

17. The method of claim 4 wherein the amino acid sequence is at least 99% identical to SEQ ID NO:8.

18. The method of claim 4 wherein the amino acid sequence is at least 99% identical to SEQ ID NO:10.

* * * * *

UNITED STATES PATENT AND TRADEMARK OFFICE
CERTIFICATE OF CORRECTION

PATENT NO. : 6,984,484 B1
APPLICATION NO. : 09/889609
DATED : January 10, 2006
INVENTOR(S) : Soloman H. Snyder et al.

It is certified that error appears in the above-identified patent and that said Letters Patent is hereby corrected as shown below:

On the title page, Inventors section (75):
 Please replace "Roscoe Brady, Jr.," with --Roscoe O. Brady, Jr.,--

On the title page, § 371 (c)(1), (2), (4) Date:
 Please replace "Dec. 12, 2001" with --Dec. 28, 2001--

Signed and Sealed this

Fifteenth Day of August, 2006

JON W. DUDAS
*Director of the United States Patent and Trademark Office*

SEQUENCE LISTING

<160> NUMBER OF SEQ ID NOS: 11

<210> SEQ ID NO 1

<211> LENGTH: 1018
<212> TYPE: DNA
<213> ORGANISM: Mus musculus

<400> SEQUENCE: 1

| | | | | | | |
|---|---|---|---|---|---|---|
| atgtgtgctc | agtactgcat | ctcctttgct | gatgttgaaa | agctcatat | caacattcaa | 60 |
| gactctatcc | acctcacccc | agtgctaaca | agctccattt | tgaatcaaat | agcagggcgc | 120 |
| aatcttttct | tcaaatgtga | gctcttccag | aaaactgggt | cttttaagat | tcgaggtgcc | 180 |
| cttaatgcca | tcagaggctt | aattcctgac | acgccagaag | agaagcccaa | agccgtagtt | 240 |
| actcacagca | gcggaaaacca | tggccaagct | ctcacctatg | ctgctaaact | ggaaggaatt | 300 |
| cctgcttaca | ttgtggttcc | ccaaacagct | cccaactgca | agaaactggc | aatccaagcc | 360 |
| tatggagcat | cgatagtata | ctgtgaccca | agtgacgagt | ccagagaaaa | ggtcactcaa | 420 |
| agaattatgc | agaaaacaga | aggcatcttg | gtccatccca | accaggagcc | tgcagtgata | 480 |
| gctggacaag | gaacaattgc | cctggaagtg | ctgaaccagg | ttcccttggt | agatgcactg | 540 |
| gtggtaccag | taggaggagg | aggaatggtt | gctggaatag | ccattacaat | taaggccctg | 600 |
| aaacctagtg | tgaaggtata | cgctgctgag | ccctcgaatg | cagatgactg | ctaccagtct | 660 |
| aaactgaaag | gagaactgac | ccccaatctt | catcctccag | aaaccatagc | agatggtgtc | 720 |
| aaatccagca | ttggcttgaa | tacctggcct | attataagag | accttgtgga | tgatgtcttc | 780 |
| actgtcaccg | aagatgaaat | caagtatgca | acccagctgg | tgtgggggag | aatgaaactg | 840 |
| ctcattgagc | cgactgctgg | cgtggcactg | gctgcagtgc | tgtctcagca | tttccaaaca | 900 |
| gtctctccag | aagtaaagaa | cgtctgcatt | gtactcagtg | ggggaatgt | agacctaacc | 960 |
| tccctgaact | gggtgggca | ggctgaacgg | ccagctcctt | accagacggt | ctgtttaa | 1018 |

<210> SEQ ID NO 2
<211> LENGTH: 608
<212> TYPE: DNA
<213> ORGANISM: Homo sapiens
<220> FEATURE:
<221> NAME/KEY: misc_feature
<222> LOCATION: (1)...(608)
<220> FEATURE:
<221> NAME/KEY: misc_feature
<222> LOCATION: (1)...(608)
<223> OTHER INFORMATION: n = A,T,C or G

<400> SEQUENCE: 2

| | | | | | | |
|---|---|---|---|---|---|---|
| ggcgcggcgc | cgatgagctg | agaaccatgt | gtgctcagta | ttgcatctcc | tttgctgatg | 60 |
| ttgaaaaagc | tcatatcaac | attcgagatt | ctatccacct | cacaccagtg | ctaacaagct | 120 |
| ccattttgaa | tcaactaaca | gggcgcaatc | ttttcttcaa | atgtgaactc | ttccagaaaa | 180 |
| caggatcttt | taagattcgt | ggtgctctca | atgccgtcag | aagcttggtt | cctgatgctt | 240 |
| tagaaaggaa | gccgaaagct | gttgttactc | acagcagtgg | aaaccatggc | caggctctca | 300 |
| cctatgctgc | caaattggaa | ggaattcctg | cttatattgt | ggtgccccag | acagctccag | 360 |
| actgtaaaaa | acttgcaata | caagcctacg | gagcgtcaat | tgtatactgt | gaacctagtg | 420 |
| atgaagtcca | gagaaaatgt | tgcaaaaagg | agttacagaa | gaaacagaag | gcatcatggt | 480 |
| acatcccaac | caggaacctg | cagtgatagc | tggacaaggg | acaattgccc | tggaagtgct | 540 |
| gaaccaggtt | cctttggtgg | atccactggt | ggncccctgta | ggtggaagga | ggaatgcttg | 600 |
| ccgggaat | | | | | | 608 |

<210> SEQ ID NO 3

```
<211> LENGTH: 509
<212> TYPE: DNA
<213> ORGANISM: Homo sapiens
<220> FEATURE:
<221> NAME/KEY: misc_feature
<222> LOCATION: (1)...(509)
<223> OTHER INFORMATION: n = A,T,C or G

<400> SEQUENCE: 3
ctgatgccca atctttatcc tccagaaacc atagcagatg gtgtcaaatc cagcattggc     60
ttgaancacc tggcctatta tcagggacct tgtggatgat atcttcactg tcacagagga   120
tgaaattaag tgtgcaaccc agctggtgtg ggagaggatg aaactactca ttgaacctac   180
agctggtgtt ggagtggctg ctgtgctgtc tcaacatttt caaactgttt ccccagaagt   240
aaagaacatt tgtattgtgc tcagtggtgg aaatgtagac ttaacctcct ccataacttg   300
ggtgaagcag gctgaaaggc cagcttctta tcagtctgtt tctgtttaat ttacagaaaa   360
ggaaatggtg ggaattcagt gtctttagat actgaagaca ttttgtttcc tagtattgtc   420
aactcttagt tatcagattc ttaatggaga gtggctattt cattaaggtt taatagttttt  480 ttttggacta agtagtggaa aaactttta                                      509

<210> SEQ ID NO 4
<211> LENGTH: 32
<212> TYPE: DNA
<213> ORGANISM: Mus musculus

<400> SEQUENCE: 4
acgcgtcgac caccatgtgt gctcagtact gc                                   32

<210> SEQ ID NO 5
<211> LENGTH: 34
<212> TYPE: DNA
<213> ORGANISM: Mus musculus

<400> SEQUENCE: 5
ataagaatgc ggccgcttaa acagaaaccg tctg                                 34

<210> SEQ ID NO 6
<211> LENGTH: 27
<212> TYPE: PRT
<213> ORGANISM: Rat rattus

<400> SEQUENCE: 6

Leu Leu Ile Glu Pro Thr Ala Gly Val Gly Leu Ala Ala Val Leu Ser
 1               5                  10                  15

Gln His Phe Gln Thr Val Ser Pro Glu Val Lys
            20                  25

<210> SEQ ID NO 7
<211> LENGTH: 25
<212> TYPE: PRT
<213> ORGANISM: Rat rattus

<400> SEQUENCE: 7

His Leu Asn Ile Gln Asp Ser Val His Leu Thr Pro Val Leu Thr Ser
 1               5                  10                  15

Ser Ile Leu Asn Gln Ile Ala Gly Arg
            20                  25

<210> SEQ ID NO 8
<211> LENGTH: 339
```

<212> TYPE: PRT
<213> ORGANISM: Mus musculus

<400> SEQUENCE: 8

```
Met Cys Ala Gln Tyr Cys Ile Ser Phe Ala Asp Val Glu Lys Ala His
  1               5                  10                  15
Ile Asn Ile Gln Asp Ser Ile His Leu Thr Pro Val Leu Thr Ser Ser
             20                  25                  30
Ile Leu Asn Gln Ile Ala Gly Arg Asn Leu Phe Phe Lys Cys Glu Leu
         35                  40                  45
Phe Gln Lys Thr Gly Ser Phe Lys Ile Arg Gly Ala Leu Asn Ala Ile
 50                  55                  60
Arg Gly Leu Ile Pro Asp Thr Pro Glu Glu Lys Pro Lys Ala Val Val
 65                  70                  75                  80
Thr His Ser Ser Gly Asn His Gly Gln Ala Leu Thr Tyr Ala Ala Lys
                 85                  90                  95
Leu Glu Gly Ile Pro Ala Tyr Ile Val Pro Gln Thr Ala Pro Asn
            100                 105                 110
Cys Lys Lys Leu Ala Ile Gln Ala Tyr Gly Ala Ser Ile Val Tyr Cys
            115                 120                 125
Asp Pro Ser Asp Glu Ser Arg Glu Lys Val Thr Gln Arg Ile Met Gln
130                 135                 140
Glu Thr Glu Gly Ile Leu Val His Pro Asn Gln Glu Pro Ala Val Ile
145                 150                 155                 160
Ala Gly Gln Gly Thr Ile Ala Leu Glu Val Leu Asn Gln Val Pro Leu
                165                 170                 175
Val Asp Ala Leu Val Val Pro Val Gly Gly Gly Gly Met Val Ala Gly
            180                 185                 190
Ile Ala Ile Thr Ile Lys Ala Leu Lys Pro Ser Val Lys Val Tyr Ala
            195                 200                 205
Ala Glu Pro Ser Asn Ala Asp Asp Cys Tyr Gln Ser Lys Leu Lys Gly
            210                 215                 220
Glu Leu Thr Pro Asn Leu His Pro Pro Glu Thr Ile Ala Asp Gly Val
225                 230                 235                 240
Lys Ser Ser Ile Gly Leu Asn Thr Trp Pro Ile Ile Arg Asp Leu Val
                245                 250                 255
Asp Asp Val Phe Thr Val Thr Glu Asp Glu Ile Lys Tyr Ala Thr Gln
            260                 265                 270
Leu Val Trp Gly Arg Met Lys Leu Leu Ile Glu Pro Thr Ala Gly Val
            275                 280                 285
Ala Leu Ala Ala Val Leu Ser Gln His Phe Gln Thr Val Ser Pro Glu
290                 295                 300
Val Lys Asn Val Cys Ile Val Leu Ser Gly Gly Asn Val Asp Leu Thr
305                 310                 315                 320
Ser Leu Asn Trp Val Gly Gln Ala Glu Arg Pro Ala Pro Tyr Gln Thr
                325                 330                 335
Val Ser Val
```

<210> SEQ ID NO 9
<211> LENGTH: 1023
<212> TYPE: DNA
<213> ORGANISM: Homo sapiens

<400> SEQUENCE: 9
atgtgtgctc agtattgcat ctcctttgct gatgttgaaa aagctcatat caacattcga    60

```
gattctatcc acctcacacc agtgctaaca agctccattt tgaatcaact aacagggcgc      120
aatcttttct tcaaatgtga actcttccag aaaacaggat cttttaagat tcgtggtgct      180
ctcaatgccg tcagaagctt ggttcctgat gctttagaaa ggaagccgaa agctgttgtt      240
actcacagca gtggaaacca tggccaggct ctcacctatg ctgccaaatt ggaaggaatt      300
cctgcttata ttgtggtgcc ccagacagct ccagactgta aaaaacttgc aatacaagcc      360
tacggagcgt caattgtata ctgtgaacct agtgatgagt ccagagaaaa tgttgcaaaa      420
agagttacag aagaaacaga aggcatcatg gtacatccca accaggagcc tgcagtgata      480
gctggacaag ggacaattgc cctggaagtg ctgaaccagg ttcctttggt ggatgcactg      540
gtggtacctg taggtggagg aggaatgctt gctggaatag caattacagt taaggctctg      600
aaacctagtg tgaaggtata tgctgctgaa ccctcaaatg cagatgactg ctaccagtcc      660
aagctgaagg ggaaactgat gcccaatctt tatcctccag aaaccatagc agatggtgtc      720
aaatccagca ttggcttgaa cacctggcct attatcaggg accttgtgga tgatatcttc      780
actgtcacag aggatgaaat taagtgtgca acccagctgg tgtgggagag atgaaaacta      840
ctcattgaac ctacagctgg tgttggagtg gctgctgtgc tgtctcaaca ttttcaaact      900
gtttccccag aagtaaagaa catttgtatt gtgctcagtg gtggaaatgt agacttaacc      960
tcctccataa cttgggtgaa gcaggctgaa aggccagctt cttatcagtc tgtttctgtt     1020
taa                                                                   1023
```

<210> SEQ ID NO 10
<211> LENGTH: 340
<212> TYPE: PRT
<213> ORGANISM: Homo sapiens

<400> SEQUENCE: 10

```
Met Cys Ala Gln Tyr Cys Ile Ser Phe Ala Asp Val Glu Lys Ala His
  1               5                  10                  15

Ile Asn Ile Arg Asp Ser Ile His Leu Thr Pro Val Leu Thr Ser Ser
                 20                  25                  30

Ile Leu Asn Gln Leu Thr Gly Arg Asn Leu Phe Phe Lys Cys Glu Leu
             35                  40                  45

Phe Gln Lys Thr Gly Ser Phe Lys Ile Arg Gly Ala Leu Asn Ala Val
         50                  55                  60

Arg Ser Leu Val Pro Asp Ala Leu Glu Arg Lys Pro Lys Ala Val Val
 65                  70                  75                  80

Thr His Ser Ser Gly Asn His Gly Gln Ala Leu Thr Tyr Ala Ala Lys
                 85                  90                  95

Leu Glu Gly Ile Pro Ala Tyr Ile Val Val Pro Gln Thr Ala Pro Asp
                100                 105                 110

Cys Lys Lys Leu Ala Ile Gln Ala Tyr Gly Ala Ser Ile Val Tyr Cys
            115                 120                 125

Glu Pro Ser Asp Glu Ser Arg Glu Asn Val Ala Lys Arg Val Thr Glu
        130                 135                 140

Glu Thr Glu Gly Ile Met Val His Pro Asn Gln Glu Pro Ala Val Ile
145                 150                 155                 160

Ala Gly Gln Gly Thr Ile Ala Leu Glu Val Leu Asn Gln Val Pro Leu
                165                 170                 175

Val Asp Ala Leu Val Val Pro Val Gly Gly Gly Gly Met Leu Ala Gly
            180                 185                 190
```

-continued

```
Ile Ala Ile Thr Val Lys Ala Leu Lys Pro Ser Val Lys Val Tyr Ala
        195                 200                 205
Ala Glu Pro Ser Asn Ala Asp Asp Cys Tyr Gln Ser Lys Leu Lys Gly
    210                 215                 220
Lys Leu Met Pro Asn Leu Tyr Pro Pro Glu Thr Ile Ala Asp Gly Val
225                 230                 235                 240
Lys Ser Ser Ile Gly Leu Asn Thr Trp Pro Ile Ile Arg Asp Leu Val
                245                 250                 255
Asp Asp Ile Phe Thr Val Thr Glu Asp Glu Ile Lys Cys Ala Thr Gln
            260                 265                 270
Leu Val Trp Glu Arg Met Lys Leu Leu Ile Glu Pro Thr Ala Gly Val
        275                 280                 285
Gly Val Ala Ala Val Leu Ser Gln His Phe Gln Thr Val Ser Pro Glu
    290                 295                 300
Val Lys Asn Ile Cys Ile Val Leu Ser Gly Gly Asn Val Asp Leu Thr
305                 310                 315                 320
Ser Ser Ile Thr Trp Val Lys Gln Ala Glu Arg Pro Ala Ser Tyr Gln
                325                 330                 335
Ser Val Ser Val
```

<210> SEQ ID NO 11
<211> LENGTH: 1670
<212> TYPE: DNA
<213> ORGANISM: Mus musculus

<400> SEQUENCE: 11

```
gaccttacac cctttgccac actggtcctg ggccaagatg ggccaatcaa agtccttacc      60
cagaattttt tgaactgaaa ttgagagaga atccctcttc agtatggaag ccataaaatg     120
taaaacacag gagctgtcag cagccatgtg tcctgcagta cggagccagc tggtctgctg     180
tgagaaggaa gccgccgtgc cagaggcagc agagaaccat gtgtgctcag tactgcatct     240
cctttgctga tgttgaaaaa gctcatatca acattcaaga ctctatccac ctcaccccag     300
tgctaacaag ctccattttg aatcaaatag cagggcgcaa tcttttcttc aaatgtgagc     360
tcttccagaa aactgggtct tttaagattc gaggtgccct taatgccatc agaggcttaa     420
ttcctgacac gccagaagag aagcccaaag ccgtagttac tcacagcagc ggaaaccatg     480
gccaagctct cacctatgct gctaaactgg aaggaattcc tgcttacatt gtggttcccc     540
aaacagctcc caactgcaag aaactggcaa tccaagccta tggagcatcg atagtatact     600
gtgacccaag tgacgagtcc agagaaaagg tcactcaaag aattatgcaa gaaacagaag     660
gcatcttggt ccatcccaac caggagcctg cagtgatagc tggacaagga acaattgccc     720
tggaagtgct gaaccaggtt cccttggtag atgcactggt ggtaccagta ggaggaggag     780
gaatggttgc tggaatagcc attacaatta aggccctgaa acctagtgtg aaggtatacg     840
ctgctgagcc ctcgaatgca gatgactgct accagtctaa actgaaagga gaactgaccc     900
ccaatcttca tcctccagaa accatagcag atggtgtcaa atccagcatt ggcttgaata     960
cctggcctat tataagagac cttgtggatg atgtcttcac tgtcaccgaa gatgaaatca    1020
agtatgcaac ccagctggtg tgggggagaa tgaaactgct cattgagccg actgctggcg    1080
tggcactggc tgcagtgctg tctcagcatt tccaaacagt ctctccagaa gtaaagaacg    1140
tctgcattgt actcagtggg gggaatgtag acctaacctc cctgaactgg gtggggcagg    1200
ctgaacggcc agctccttac cagacggtct gtttaaattc aggcaagatt gtctctagat    1260
```

```
gaaaattttg tttccatctt ccctttaaaa attatgttca aaatcctaat gaagaaagtg    1320
taagtaatca tgtaaattct gtacttagca gagacatgga caactgaaat acagagcaca    1380
agctgcctgg tcacaaccca gactccaaca ctggagtttt ggttggttgc agtagagaca    1440
gaacccaact gagtctctta ctccatgtct acttcagaca ctgttgaaga gatgtcactt    1500
ttaacccaag gtactggctc tggtacatat gggtcataag tccacttggg aaatactcgc    1560
ttatagagat tcattaatac tgtgtcctga gatttcagct ttccccatca aaactgcact    1620
ttatatggcc atgggtacct aaaagttaaa acagataatt ggtcaaaaat                1670
```